US010376495B2

(12) United States Patent
Sanchez-Ramos et al.

(10) Patent No.: US 10,376,495 B2
(45) Date of Patent: Aug. 13, 2019

(54) SMALL MOLECULES THAT MIMIC OR ANTAGONIZE ACTIONS OF GRANULOCYTE COLONY-STIMULATING-FACTOR (G-CSF)

(71) Applicants: UNIVERSITY OF SOUTH FLORIDA, Tampa, FL (US); THE UNITED STATES GOVERNMENT AS REPRESENTED BY THE DEPARTMENT OF VETERANS AFFAIRS, Washington, DC (US); H. LEE MOFFITT CANCER CENTER AND RESEARCH INSTRITUTE INC., Tampa, FL (US)

(72) Inventors: Juan Sanchez-Ramos, Plant City, FL (US); Vasyl Sava, Wesley Chapel, FL (US); Shijie Song, Tampa, FL (US); Said Sebti, Tampa, FL (US)

(73) Assignees: University of South Florida, Tampa, FL (US); The United States Government as Represented by the Department of Veterans, Washington, DC (US); H. Lee Moffitt Cancer Center and research Institute Inc., Tampa, FL (US)

(*) Notice: Subject to any disclaimer, the term of this patent is extended or adjusted under 35 U.S.C. 154(b) by 0 days.

(21) Appl. No.: 15/821,634

(22) Filed: Nov. 22, 2017

(65) Prior Publication Data
US 2018/0177763 A1 Jun. 28, 2018

Related U.S. Application Data

(60) Provisional application No. 62/426,032, filed on Nov. 23, 2016.

(51) Int. Cl.
*A61K 31/4174* (2006.01)
*C07D 233/60* (2006.01)
*A61K 31/53* (2006.01)
*A61K 38/19* (2006.01)
*A61P 25/28* (2006.01)

(52) U.S. Cl.
CPC .......... *A61K 31/4174* (2013.01); *A61K 31/53* (2013.01); *A61K 38/193* (2013.01); *A61P 25/28* (2018.01); *C07D 233/60* (2013.01)

(58) Field of Classification Search
CPC .. A61K 31/4174; A61K 31/53; A61K 38/193; A61P 25/28; C07D 233/60
USPC ...................................................... 514/396
See application file for complete search history.

(56) References Cited

U.S. PATENT DOCUMENTS

| | | |
|---|---|---|
| 4,554,101 A | 11/1985 | Hopp |
| 5,580,859 A | 12/1996 | Feigner et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Feigner et al. |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,302,874 B1 | 10/2001 | Zhang et al. |
| 7,664,545 B2 | 2/2010 | Westersten et al. |
| 2011/0319459 A1* | 12/2011 | Gupta ................ A61K 31/4164 514/397 |

OTHER PUBLICATIONS

Acosta et al., "Combination therapy of human umbilical cord blood cells and granulocyte colony stimulating factor reduces histopathological and motor impairments in an experimental model of chronic traumatic brain injury," PLoS One, 2014, 9(3):e90953.
Apostolatos et al., "Vitamin A Metabolite, All-trans-retinoic Acid, Mediates Alternative Splicing of Protein Kinase C δVIII (PKCδVIII) Isoform via Splicing Factor SC35," J. Biol. Chem., 2010, 285, 25987-25995.
Bussolino et al., "Granulocyte- and granulocyte-macrophage-colony stimulating factors induce human endothelial cells to migrate and proliferate," Nature, 1989, 337(6206):471-3.
Chen et al., "Recombinant human granulocyte colony-stimulating factor enhanced the resolution of venous thrombi," J Vasc Surg, 2008, 47(5):1058-1065.
Dale, "Current management of chemotherapy-induced neutropenia: the role of colony-stimulating factors," Semin Oncol, 2003, 30(4 Suppl 13):3-9.
Diederich et al., "Synergetic effects of granulocyte-colony stimulating factor and cognitive training on spatial learning and survival of newborn hippocampal neurons," PLoS One, 2009, 4(4):e5303.
Diederich et al., "The role of granulocyte-colony stimulating factor (G-CSF) in the healthy brain: a characterization of G-CSF-deficient mice," J Neurosci, 2009, 29(37):11572-11581.
Dong et al., "Activation of Akt kinase by granulocyte colony-stimulating factor (G-CSF): evidence for the role of a tyrosine kinase activity distinct from the Janus kinases," Blood, 2000, 95(5):1656-1662.

(Continued)

*Primary Examiner* — Kristin A Vajda
(74) *Attorney, Agent, or Firm* — Michael Best & Friedrich LLP

(57) ABSTRACT

Described herein are compound for the modulation of the G-CSF receptor. The compounds may act as agonists, antagonists, and/or mixed or partial agonists/antagonists of G-CSF. Further provided herein are methods of treating a condition, including, for example, a neurodegenerative disease, by administering a compound as detailed herein.

12 Claims, 15 Drawing Sheets

Specification includes a Sequence Listing.

(56) References Cited

OTHER PUBLICATIONS

Donnelly et al., "DNA vaccines," Ann. Rev. Immunol., 1997, 15:617-648.
Dower et al., "Detection and characterization of high affinity plasma membrane receptors for human interleukin 1," J Exp Med, 1985, 162(2):501-515.
Hanazono et al., "Structural analysis of the receptors for granulocyte colony-stimulating factor on neutrophils," Exp Hematol, 1990, 18(10):1097-103.
Heagerty et al., "Time-dependent ROC curves for censored survival data and a diagnostic marker," Biometrics, 2000, 56(2):337-344.
Honjo et al., "Crystallization of a 2:2 complex of granulocyte-colony stimulating factor (GCSF) with the ligand-binding region of the GCSF receptor," Acta Crystallogr Sect F Struct Biol Cryst Commun, 2005, 61(Pt 8):788-790.
Hunter et al., "Phosphatidylinositol 3'-kinase and SH2-containing inositol phosphatase (SHIP) are recruited by distinct positive and negative growth-regulatory domains in the granulocyte colony-stimulating factor receptor," J Immunol, 1998, 160(10):4979-4987.
Jiang et al., "Identification of a Novel Antiapoptotic Human Protein Kinase C delta Isoform, PKCdeltaVlll in NT2 Cells," Biochemistry, 2008, 47(2):787-797.
Kondo et al., "Human granulocyte colony-stimulating factor receptors in acute myelogenous leukemia," Eur J Haematol, 1991, 46(4):223-230.
Kusano et al., "A potential therapeutic role for small nonpeptidyl compounds that mimic human granulocyte colony-stimulating factor," Blood, 2004, 103(3):836-842.
Kyte et al., "A Simple Method for Displaying the Hydropathic Character of a Protein," J. Mol. Biol. 1982, 157, 105-132.
Morikawa et al., "Characterization of granulocyte colony-stimulating factor receptor expressed on human lymphocytes," Br J Haematol, 2002, 118(1):296-304.
Patel et al., "PKCδ Alternatively Spliced Isoforms Modulate Cellular Apoptosis in Retinoic Acid-Induced Differentiation of Human NT2 Cells and Mouse Embryonic Stem Cells," Gene Expression 2006, 13(2):73-84.
Pennington et al., "Direct Actions of Granulocyte-Colony Stimulating Factor on Huma nNeuronal and Monocytic Cell Lines," Alzheimer's Disease and Parkinsonism, 2013, 3(2):121.
Pitzer et al., "Granulocyte-colony stimulating factor improves outcome in a mouse model of amyotrophic lateral sclerosis," Brain, 2008, 131(Pt 12):3335-3347.
Pusic et al., "The use of growth factors in hematopoietic stem cell transplantation," Curr Pharm Des, 2008, 14(20):1950-1961.
Sanchez-Ramos et al., "Granulocyte colony stimulating factor decreases brain amyloid burden and reverses cognitive impairment in Alzheimer's mice," Neuroscience, 2009, 163(1):55-72.
Sanchez-Ramos et al., "Pilot Study of Granulocyte-Colony Stimulating Factor for Treatment of Alzheimer's Disease," Journal of Alzheimers Disease, 2012, 31(4):843-855.
Sanchez-Ramos et al., "The potential of hematopoietic growth factors for treatment of Alzheimer's disease: a mini-review," BMC Neurosci, 2008, 9 Suppl 2:S3.
Schäbitz et al., "New targets for established proteins: exploring G-CSF for the treatment of stroke," Trends Pharmacol Sci, 2007. 28(4):157-161.
Schneider et al., "A role for G-CSF (Granulocyte-colony stimulating factor) in the central nervous system," Cell Cycle, 2005, 4(12):1753-1757.
Schneider et al., "The hematopoietic factor G-CSF is a neuronal ligand that counteracts programmed cell death and drives neurogenesis," Journal of Clinical Investigation, 2005, 115(8):2083-2098.
Shimoda et al., "Identification of a functional receptor for granulocyte colony-stimulating factor on platelets," Journal of Clinical Investigation, 1993, 91(4):1310-1313.
Shors et al., "Neurogenesis in the adult is involved in the formation of trace memories," Nature 2001, 410, 372-376.
Shors et al., "Neurogenesis may relate to some but not all types of hippocampal-dependent learning," Hippocampus, 2002, 12(5):578-584.
Song et al., "Granulocyte colony-stimulating factor promotes behavioral recovery in a mouse model of traumatic brain injury," J Neurosci Res, 2016, 94(5):409-423.
Song et al., "Granulocyte-colony stimulating factor (G-CSF) enhances recovery in mouse model of Parkinson's disease," Neurosci Lett, 2011, 487(2):153-157.
Song et al., "Granulocyte-colony stimulating factor promotes brain repair following traumatic brain injury by recruitment of microglia and increasing neurotrophic factor expression," Restor Neurol Neurosci, 2016, 34(3):415-431.
Tamada et al., "Homodimeric cross-over structure of the human granulocyte colony-stimulating factor (GCSF) receptor signaling complex," Proc Natl Acad Sci U S A, 2006, 103(9):3135-3140.
Tian et al., "A small, nonpeptidyl mimic of granulocyte-colony-stimulating factor," Science, 1998, 281(257):257-259.
Tian et al., "Rapid activation of the STAT3 transcription factor by granulocyte colony-stimulating factor," Blood, 1994, 84(6):1760-1764.
Vorhees et al., "Morris water maze: procedures for assessing spatial and related forms of learning and memory," Nat. Protoc., 2006, 1(2):848-858.
Xie et al., "SH-SY5Y human neuroblastoma cell line: in vitro cell model of dopaminergic neurons in Parkinson's disease," Chin Med J (Engl), 2010, 123(8):1086-1092.
Yang et al., "Granulocyte colony-stimulating factor enhances cellular proliferation and motor function recovery on rats subjected to traumatic brain injury," Neurol Res, 2010, 32(10):1041-1049.
Yata et al., "Granulocyte-colony stimulating factor inhibits apoptotic neuron loss after neonatal hypoxia-ischemia in rats," Brain Research, 2007, 1145(1):227-238.

* cited by examiner

SMALL MOLECULES THAT MIMIC OR ANTAGONIZE ACTIONS OF GRANULOCYTE COLONY-STIMULATING-FACTOR (G-CSF)

CROSS-REFERENCE TO RELATED APPLICATION(S)

This application claims priority to U.S. Provisional Patent Application No. 62/426,032, filed Nov. 23, 2016, which is incorporated herein by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 11,580 Byte ASCII (Text) file named "16B135-210112-9006-US01-SEQ-LIST-11-22-17.txt" created on Nov. 22, 2017.

FIELD

This disclosure relates to Granulocyte Colony-Stimulating Factor (G-CSF) and treatments for neurodegenerative disease.

INTRODUCTION

Granulocyte colony-stimulating factor (G-CSF) is a hematopoietic cytokine commonly used for treatment of neutropenia and to increase generation of hematopoietic stem/progenitor cells in bone marrow donors. G-CSF also exerts direct effects on neural stem/progenitor cells and is expressed, along with its receptor G-CSF-R, in neurogenic zones of the hippocampus (HC), the sub-ventricular zone, and the olfactory bulb. The G-CSF receptor and its ligand are also expressed by mature neurons in several other areas of the brain including pyramidal cells in cortical layers (specifically II and V), entorhinal cortex, Purkinje cells of the cerebellum, and in cerebellar nuclei in rats. The G-CSF receptor is common and can be found on the cell surfaces of endothelial cells, lymphocytes, platelets, and neutrophils.

The role of G-CSF as a neurotrophic factor during development and in adult life is increasingly recognized. Mice bred to have a deficiency in G-CSF were reported to have problems with memory formation and development of motor skills. More specifically, the hippocampus from these mice exhibited deficits in the induction of long term potentiation in the CA1 region, decreased neuronal precursor cells in the dentate gyrus (DG), and decreased dendritic complexity in neurons in the DG and CA1 region of the HC. The defects seen in G-CSF deficient mice support the designation of G-CSF as a true neurotrophic factor, playing a role in neurogenesis and the maintenance of structural and functional integrity of the hippocampal formation. In combination with cognitive training, G-CSF can also significantly improve spatial learning and new neuron survival in the hippocampus.

The recognition that G-CSF acts directly on neural tissue has stimulated research on the therapeutic applications of these agents for neurodegenerative diseases, stroke, and brain trauma. G-CSF administration was reported to decrease amyloid burden, enhance neurogenesis, synaptogenesis, and cognitive performance in a mouse model of Alzheimer's disease (AD). Systemic G-CSF administration to rats that had sustained traumatic brain injury (TBI) resulted in significantly better motor function recovery than the control group. G-CSF administration to mice in a model of traumatic brain injury resulted in enhanced recovery of cognitive function in a hippocampal-dependent learning task. G-CSF also improves survival in a transgenic mouse model of amyotrophic lateral sclerosis (ALS). In a mouse model of AD (the transgenic APP/PS1 mouse), G-CSF treatment was effective in decreasing amyloid burden, enhancing neurogenesis, and improving performance on a hippocampal-dependent task.

Granulocyte-colony stimulating factor (G-CSF) is both a hematopoietic growth factor used clinically to treat neutropenia and a neurotrophic factor that exerts direct effects on neural cells. There are several disadvantages to the application of human G-CSF as a neurotrophic factor to treat neurologic diseases. For example, (1) human G-CSF is produced by recombinant DNA technology and may be expensive to manufacture and costly to administer as a course of treatment; (2) the primary peripheral actions of G-CSF limit the dose that can be safely administered to treat brain disorders; and (3) there are presently no known specific G-CSF receptor antagonists capable of blocking the peripheral actions of G-CSF, leaving intact the direct neurotrophic effects in brain. Small molecule mimetics of G-CSF are highly sought as potential drugs for neurodegenerative diseases, stroke, and brain injury trauma.

SUMMARY

In an aspect, the disclosure relates to methods of treating a condition in a subject. The method may include administering a compound to the subject, wherein the compound is according to Formula I:

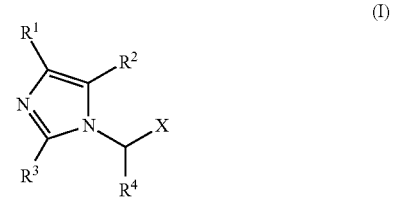

(I)

wherein $R^1$ and $R^2$ are each hydrogen, or $R^1$ and $R^2$ together with the carbon atoms to which they are attached form a phenyl ring; $R^3$ and $R^4$ are each hydrogen, or $R^3$ and $R^4$ together with the atoms to which they are attached form a six-membered heterocyclic ring, wherein the ring is unsubstituted or substituted with one substituent selected from amino, nitro, methyl, ethyl, and hydroxyl; X is —C($R^5$)($R^6$)-phenyl wherein the phenyl is substituted with $R^7$ and $R^8$, or X is indole substituted with 0, 1, 2, or 3 $R^9$, or X is pyrazole substituted with phenyl wherein the phenyl is substituted with 0, 1, 2, or 3 $R^{10}$; $R^5$ and $R^6$ are each independently selected from hydrogen, hydroxyl, $C_1$-$C_4$ alkyl, and $C_1$-$C_4$ alkoxy, or $R^5$ and $R^6$ together form an oxo group; $R^7$ is hydrogen, hydroxyl, $C_1$-$C_{12}$ alkyl, or $C_1$-$C_{12}$ alkoxy; $R^8$ is halogen, hydrogen, hydroxyl, $C_1$-$C_4$ alkyl, or $C_1$-$C_4$ alkoxy; each $R^9$ is independently halogen, hydrogen, hydroxyl, $C_1$-$C_4$ alkyl, $C_1$-$C_4$ alkoxy, amino, or nitro; and each $R^{10}$ is independently halogen, hydrogen, hydroxyl, $C_1$-$C_4$ alkyl, $C_1$-$C_4$ alkoxy, amino, or nitro, or the compound is according to Formula II:

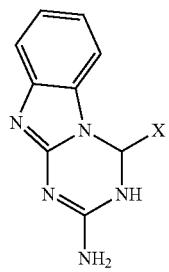

(II)

wherein X is indole substituted with 0, 1, 2, or 3 $R^9$, or X is pyrazole substituted with phenyl wherein the phenyl is substituted with 0, 1, 2, or 3 $R^{10}$; each $R^9$ is independently halogen, hydrogen, hydroxyl, $C_1$-$C_4$ alkyl, $C_1$-$C_4$ alkoxy, amino, or nitro; and each $R^{10}$ is independently halogen, hydrogen, hydroxyl, $C_1$-$C_4$ alkyl, $C_1$-$C_4$ alkoxy, amino, or nitro, or the compound is according to Formula III:

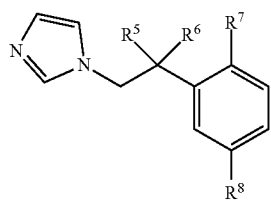

(III)

wherein $R^5$ and $R^6$ are independently hydrogen, hydroxyl, methyl, ethyl, methoxy, or ethoxy, or $R^5$ and $R^6$ together form an oxo group; $R^7$ is hydrogen, hydroxyl, $C_1$-$C_{12}$ alkyl, or $C_1$-$C_{12}$ alkoxy; and $R^8$ is halogen, hydrogen, hydroxyl, $C_1$-$C_4$ alkyl, or $C_1$-$C_4$ alkoxy, and wherein the condition is selected from the group consisting of neurodegenerative disease, stroke, traumatic brain injury (TBI), impaired motor function, and impaired cognitive function.

In some embodiments, the neurodegenerative disease is selected from the group consisting of Alzheimer's Disease (AD), amyotrophic lateral sclerosis (ALS), Parkinson's Disease (PD), prion disease, motor neuron disease, Huntington's Disease, spinocerebellar ataxia, and spinal muscular atrophy.

In a further aspect, the disclosure relates to methods of stimulating the central nervous system Granulocyte Colony-Stimulating Factor (G-CSF) Receptor in a subject. The method may include administering a compound to the subject, wherein the compound is according to Formula I:

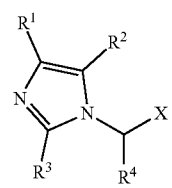

(I)

wherein $R^1$ and $R^2$ are each hydrogen, or $R^1$ and $R^2$ together with the carbon atoms to which they are attached form a phenyl ring; $R^3$ and $R^4$ are each hydrogen, or $R^3$ and $R^4$ together with the atoms to which they are attached form a six-membered heterocyclic ring, wherein the ring is unsubstituted or substituted with one substituent selected from amino, nitro, methyl, ethyl, and hydroxyl; X is —$C(R^5)(R^6)$-phenyl wherein the phenyl is substituted with $R^7$ and $R^8$, or X is indole substituted with 0, 1, 2, or 3 $R^9$, or X is pyrazole substituted with phenyl wherein the phenyl is substituted with 0, 1, 2, or 3 $R^{10}$; $R^5$ and $R^6$ are each independently selected from hydrogen, hydroxyl, $C_1$-$C_4$ alkyl, and $C_1$-$C_4$ alkoxy, or $R^5$ and $R^6$ together form an oxo group; $R^7$ is hydrogen, hydroxyl, $C_1$-$C_{12}$ alkyl, or $C_1$-$C_{12}$ alkoxy; $R^8$ is halogen, hydrogen, hydroxyl, $C_1$-$C_4$ alkyl, or $C_1$-$C_4$ alkoxy; each $R^9$ is independently halogen, hydrogen, hydroxyl, $C_1$-$C_4$ alkyl, $C_1$-$C_4$ alkoxy, amino, or nitro; and each $R^{10}$ is independently halogen, hydrogen, hydroxyl, $C_1$-$C_4$ alkyl, $C_1$-$C_4$ alkoxy, amino, or nitro, or the compound is according to Formula II:

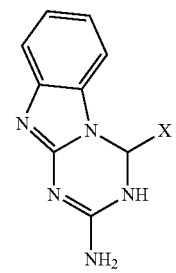

(II)

wherein X is indole substituted with 0, 1, 2, or 3 $R^9$, or X is pyrazole substituted with phenyl wherein the phenyl is substituted with 0, 1, 2, or 3 $R^{10}$; each $R^9$ is independently halogen, hydrogen, hydroxyl, $C_1$-$C_4$ alkyl, $C_1$-$C_4$ alkoxy, amino, or nitro; and each $R^{10}$ is independently halogen, hydrogen, hydroxyl, $C_1$-$C_4$ alkyl, $C_1$-$C_4$ alkoxy, amino, or nitro, or the compound is according to Formula III:

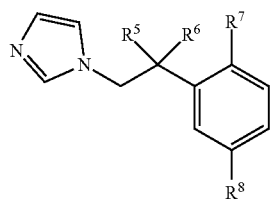

(III)

wherein $R^5$ and $R^6$ are independently hydrogen, hydroxyl, methyl, ethyl, methoxy, or ethoxy, or $R^5$ and $R^6$ together form an oxo group; $R^7$ is hydrogen, hydroxyl, $C_1$-$C_{12}$ alkyl, or $C_1$-$C_{12}$ alkoxy; and $R^8$ is halogen, hydrogen, hydroxyl, $C_1$-$C_4$ alkyl, or $C_1$-$C_4$ alkoxy.

In some embodiments, the compound is of Formula I, and wherein $R^1$ and $R^2$ are each hydrogen. In some embodiments, the compound is of Formula I, and wherein $R^1$ and $R^2$ together with the carbon atoms to which they are attached form a phenyl ring. In some embodiments, the compound is of Formula I, and wherein $R^3$ and $R^4$ are each hydrogen. In some embodiments, the compound is of Formula I, and wherein $R^3$ and $R^4$ together with the atoms to which they are attached form a six-membered heterocyclic ring, wherein the ring is unsubstituted or substituted with one substituent selected from amino, nitro, methyl, ethyl, and hydroxyl. In some embodiments, the six-membered heterocyclic ring is substituted with amino or nitro. In some embodiments, the compound is of Formula I, and wherein X is —C($R^5$)($R^6$)-phenyl wherein the phenyl is substituted with $R^7$ and $R^8$. In some embodiments, the compound is of Formula I or Formula III, and wherein $R^5$ and $R^6$ are each independently hydroxyl or methyl. In some embodiments, the compound is of Formula I or Formula III, and wherein $R^5$ and $R^6$ together form an oxo group. In some embodiments, the compound is of Formula I or Formula III, and wherein $R^7$ is hydroxyl or $C_1$-$C_{12}$ alkoxy. In some embodiments, $R^7$ is hydroxyl. In some embodiments, the compound is of Formula I or Formula III, and wherein $R^8$ is halogen. In some embodiments, halogen is Cl. In some embodiments, the compound is of Formula I or Formula II, and wherein X is indole substituted with 0, 1, 2, or 3 $R^9$. In some embodiments, each $R^9$ is independently halogen or methoxy. In some embodiments, the compound is of Formula I or Formula II, and wherein X is pyrazole substituted with phenyl, wherein the phenyl is substituted with 0, 1, 2, or 3 $R^{10}$. In some embodiments, each $R^{10}$ is independently hydroxyl, methoxy, or nitro.

In some embodiments, the compound decreases amyloid burden, enhances neurogenesis, enhances synaptogenesis, or enhances cognitive performance, or a combination thereof. In some embodiments, the compound binds the Granulocyte Colony-Stimulating Factor (G-CSF) Receptor. In some embodiments, the compound displaces at least 50% of G-CSF from the G-CSF receptor. In some embodiments, the compound displaces at least 75% of G-CSF from the G-CSF receptor. In some embodiments, the compound is a peripheral antagonist of the G-CSF receptor. In some embodiments, the compound is a central agonist of G-CSF receptor. In some embodiments, expression of Bcl2 is increased. In some embodiments, expression of PKCδVIII is increased. In some embodiments, expression of STAT3 is increased. In some embodiments, expression of Bax is decreased. In some embodiments, leukopoiesis is minimally affected or is not affected.

In some embodiments, the compound is selected from the following:

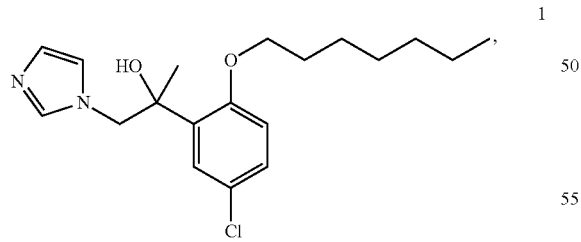
1

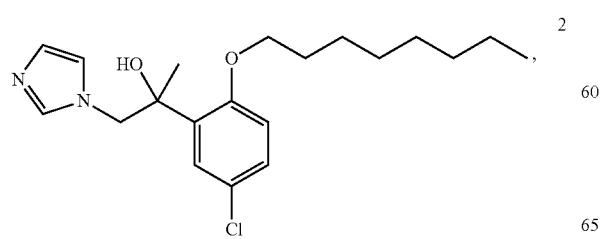
2

-continued

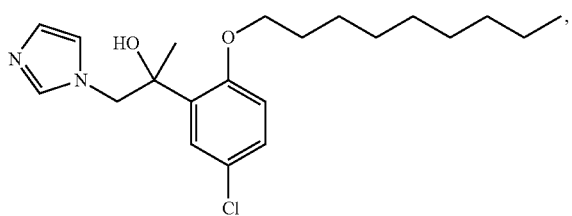
3

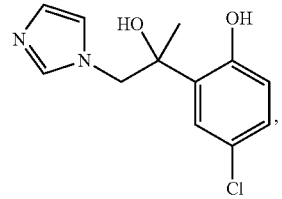
4

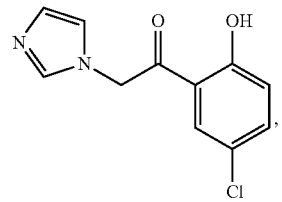
5

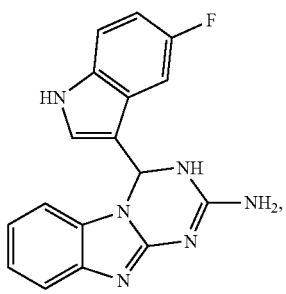
6

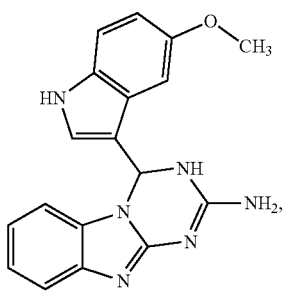
7

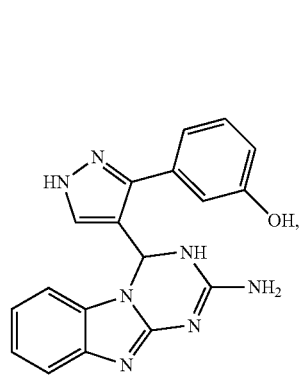
8

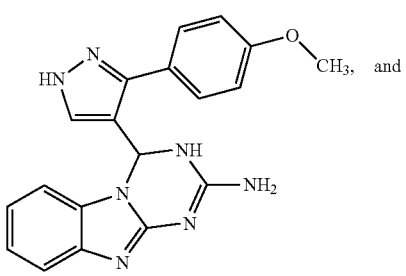

9 and

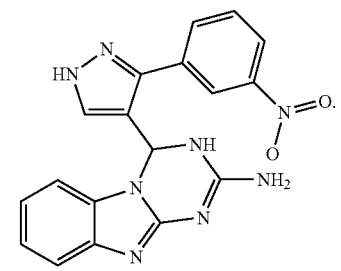

10

In some embodiments, the compound is selected from the following:

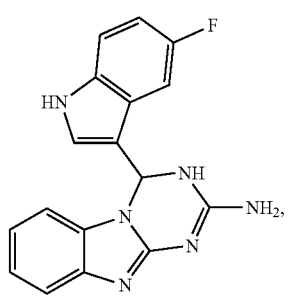

6

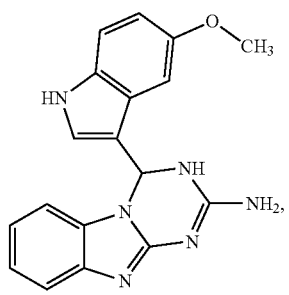

7

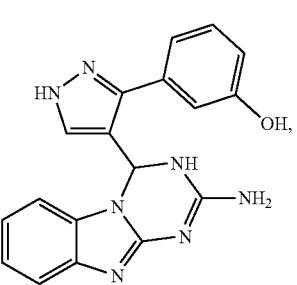

8

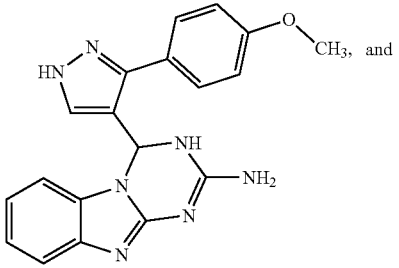

9 and

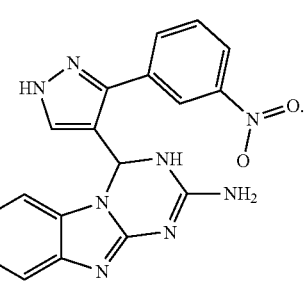

10

In some embodiments, the compound is selected from the following compounds:

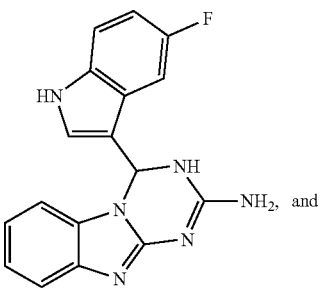

6 and

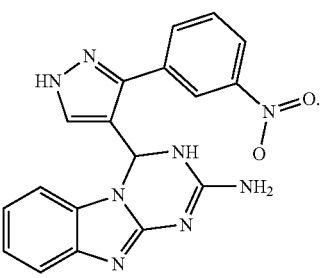

10

In some embodiments, the compound is co-administered with a G-CSF polypeptide. In some embodiments, the G-CSF polypeptide comprises an amino acid sequence of SEQ ID NO: 1. In some embodiments, the G-CSF polypeptide is encoded by a polynucleotide of SEQ ID NO: 2.

In a further aspect, the disclosure relates to a compound selected from the following:

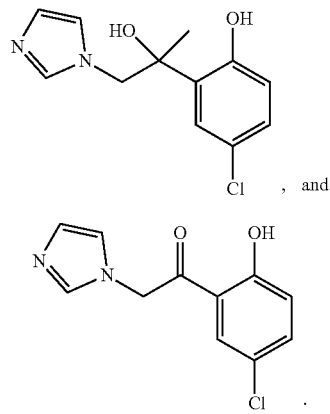

The disclosure provides for other aspects and embodiments that will be apparent in light of the following detailed description and accompanying Figures.

BRIEF DESCRIPTION OF THE DRAWINGS

(FIG. 5A) Immunoblot from cells incubated with three concentrations of Compound 6 alone and in the presence of G-CSF (100 ng/mL). (FIG. 5B) Immunoblot from cells incubated with G-CSF alone and 3 concentrations of Compound 10 alone and in the presence of G-CSF (100 ng/mL). (FIG. 5C, FIG. 5D) Densitometric analyses of Immunoblots from FIG. 5A (Compound 6) and FIG. 5B (Compound 10) respectively. (*)=p<0.05 based on one-way ANOVA of the Bcl2 data followed by Dunnett's multiple comparisons against vehicle control. (#)=p<0.05 based on one-way ANOVA of the PKCδVIII data alone followed by Dunnett's multiple comparisons against vehicle control. Insert box shows effects of co-administration of G-CSF with Compounds 6 or 10. ($)=p<0.05 based on one-way ANOVA followed by Dunnett's multiple comparisons to G-CSF alone.

(FIG. 6A) Immunoblot from cells incubated with three concentrations of Compound 6 alone and in the presence of G-CSF (100 ng/mL). (FIG. 6B) Immunoblot from cells incubated with 3 concentrations of Compound 10 alone and in the presence of G-CSF (100 ng/mL). (FIG. 6C, FIG. 6D) Densitometric analyses of Immunoblots from FIG. 6A (Compound 6) and FIG. 6B (Compound 10), respectively. (*)=p<0.05 based on one-way ANOVA of the Bcl2 data followed by Dunnett's correction for multiple comparisons against vehicle control. (#)=p<0.05) based on one-way ANOVA of the PKCδVIII data alone followed by Dunnett's correction for multiple comparisons against vehicle control. Insert box shows effects of co-administration of G-CSF with Compounds 6 or 10. (&)=p<0.05 based on one-way ANOVA of Bcl2 data followed by Dunnett's correction for multiple comparisons to G-CSF alone. ($)=p<0.05 based on one-way ANOVA of the PKCδVIII data alone followed by Dunnett's correction for multiple comparisons against G-CSF treatment.

DETAILED DESCRIPTION

Figure 1:
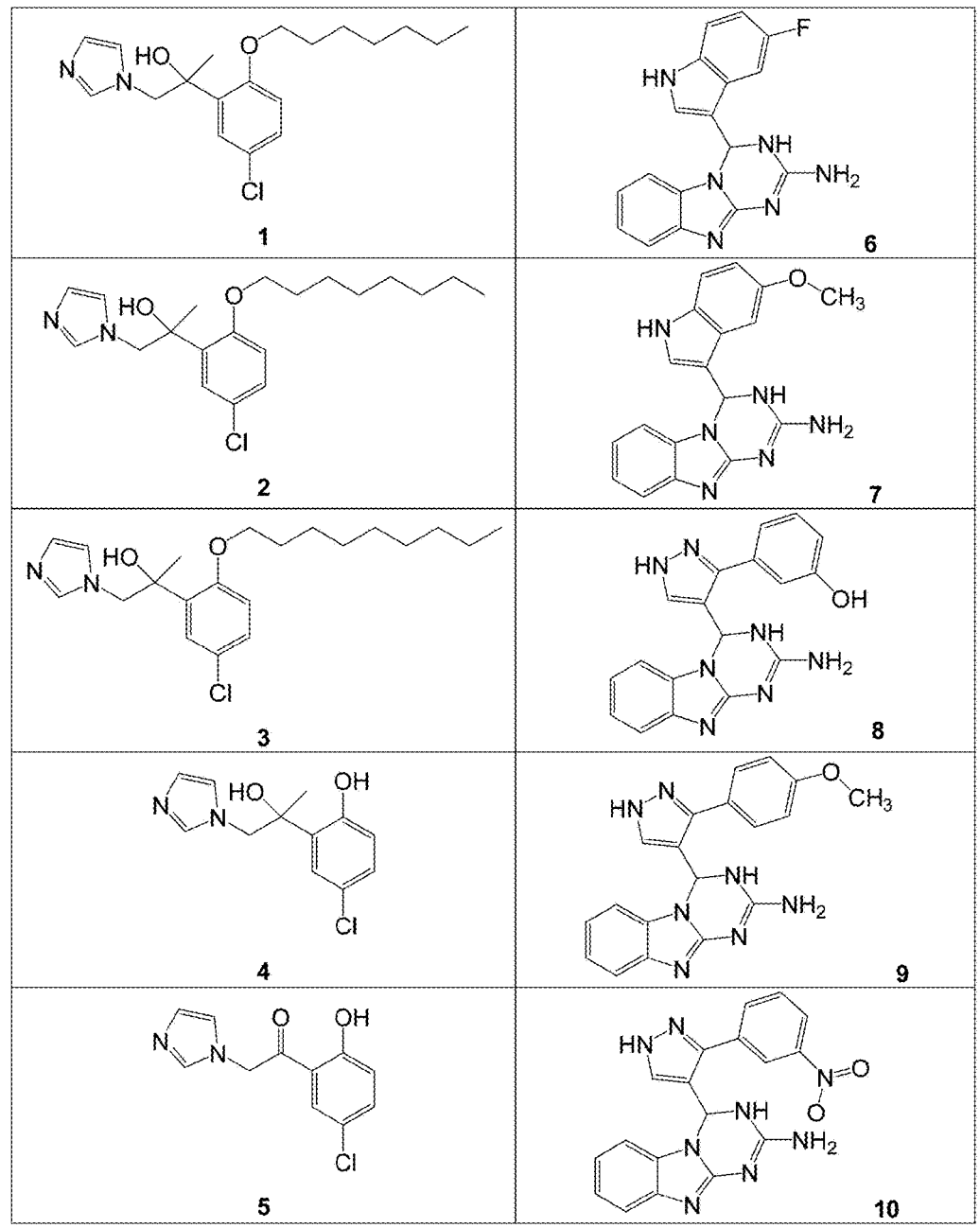
FIG. 1. Chemical structures of ten small molecules with potential to interact with the G-CSF receptor.
Figure 2:
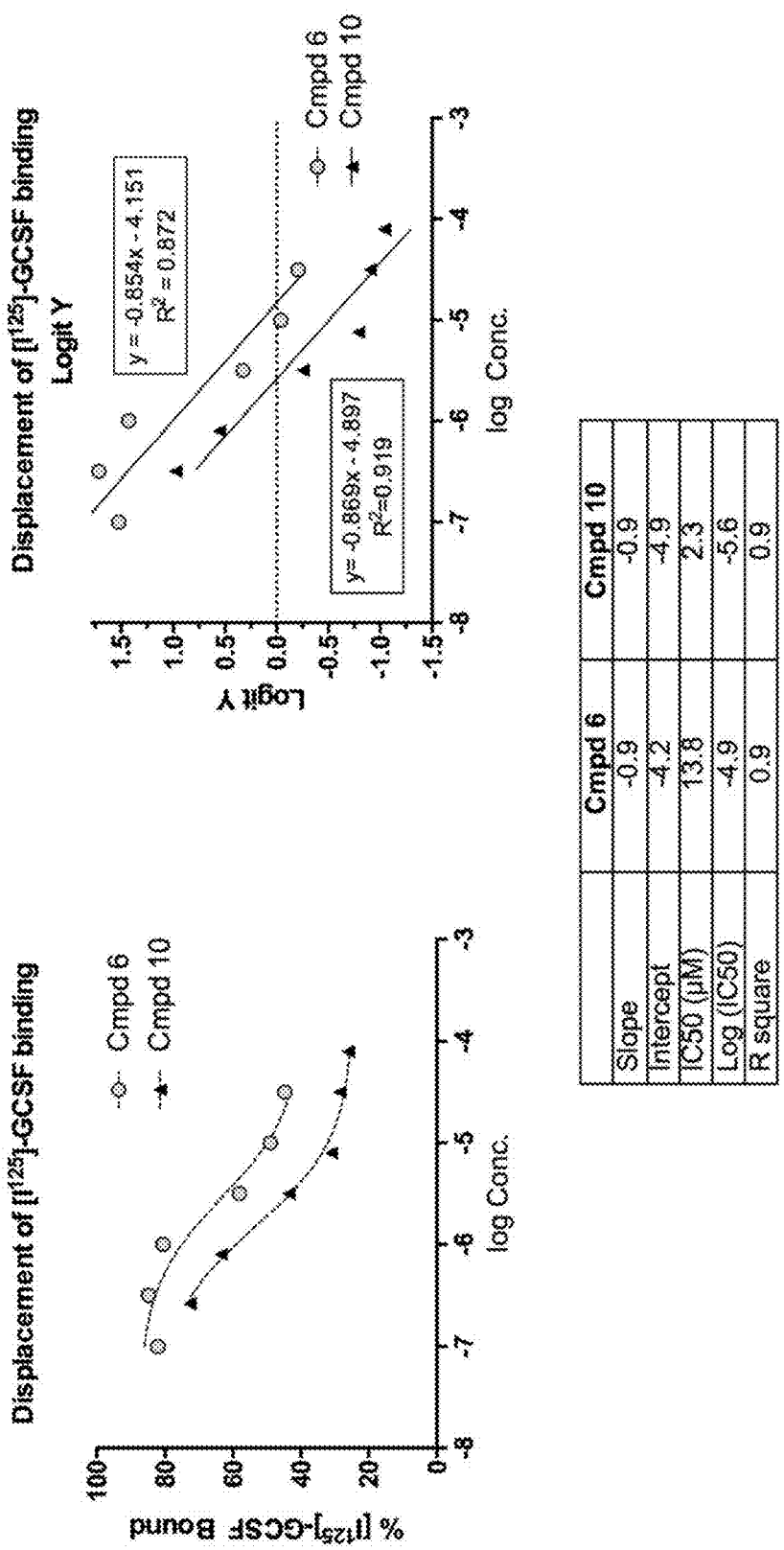
FIG. 2. Compounds 6 and 10 displaced radio-labeled G-CSF from receptor expressed on human monocytes. Results are based on the mean of two separate experiments with replicates of three within each experiment. Panel on the left shows percent of radio-labeled G-CSF bound to receptor in the presence of increasing concentrations of Compound 6 and Compound 10. Right panel shows Logit Y (logistic regression analysis) vs concentrations of Compounds 6 and 10. Insert shows parameters of competitive binding for Compound 6 (13.7 nM) and Compound 10 (2.3 nM).
Figure 3A:
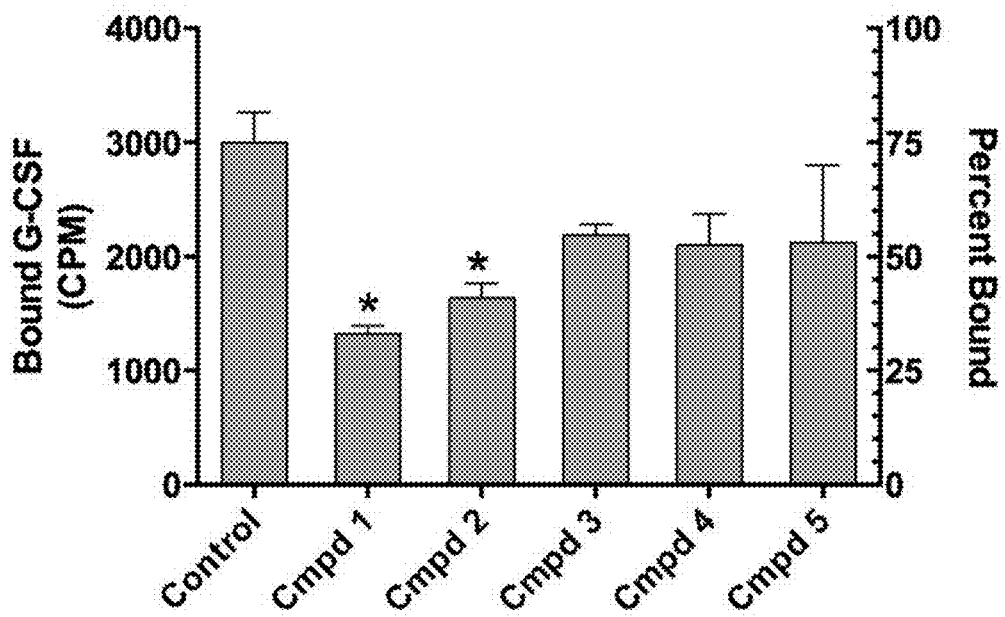
FIG. 3A and FIG. 3B. Displacement of $[I^{125}]$-G-CSF from its receptor expressed on monocytes by Compounds 1-10. The Y-axis in FIG. 3A shows amount of bound G-CSF in CPM and the Y-axis in FIG. 3B indicates percent of the radiolabeled G-CSF bound to receptor. (*) Indicates significant displacement p<0.05. Compound 10 was the most effective, displacing 86.6% of $I^{125}$-G-CSF from its receptor.
Figure 3B:
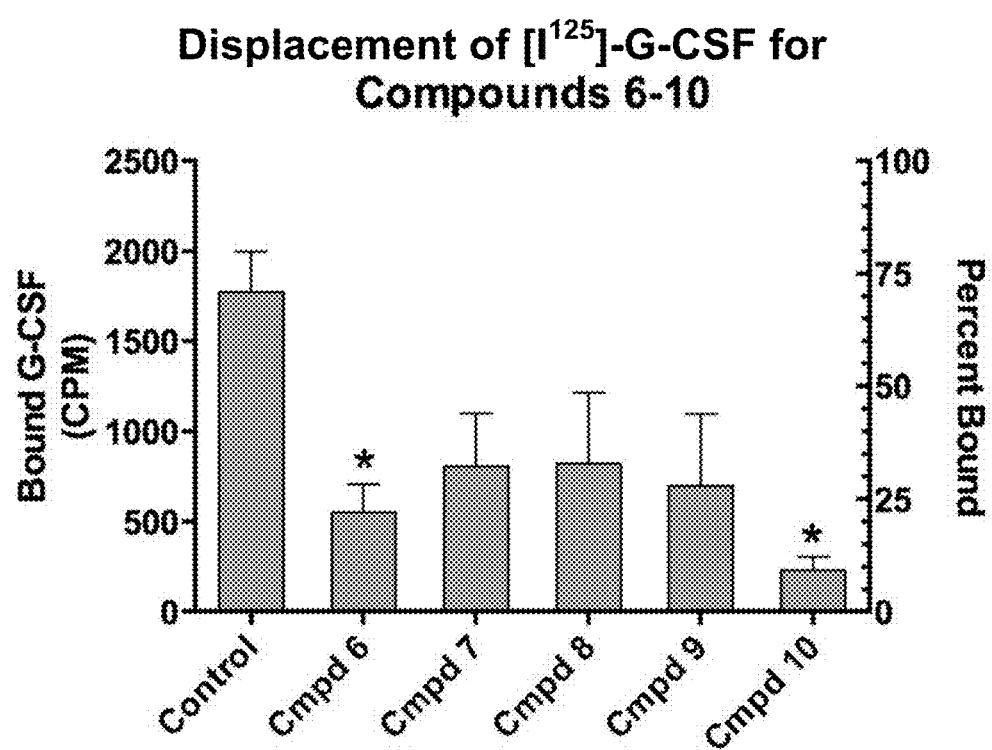
Figure 4A:
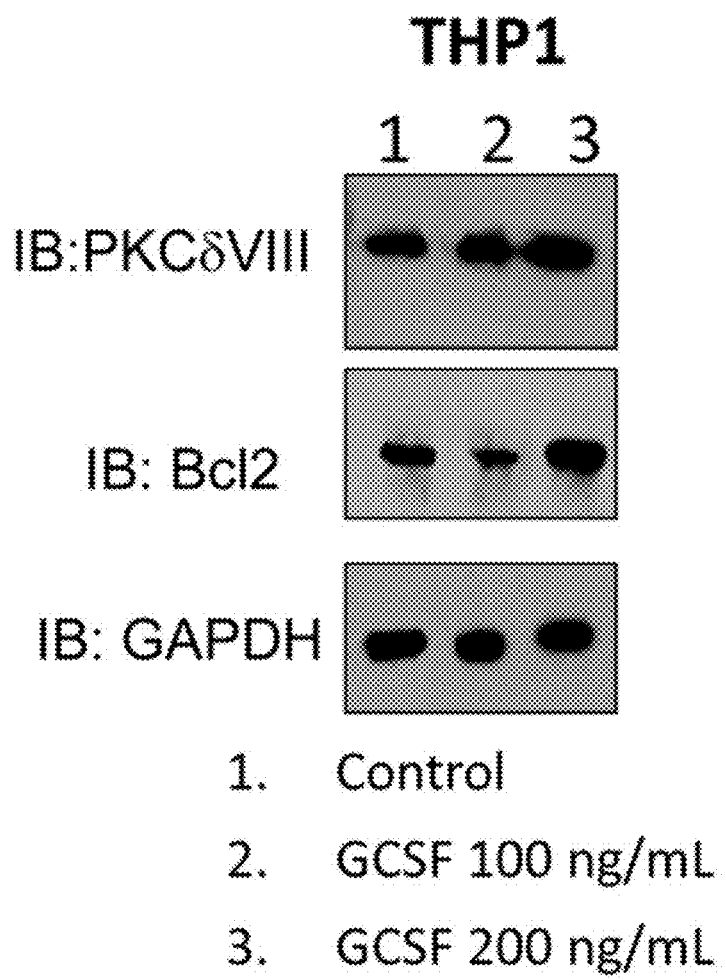
FIG. 4A, FIG. 4B, FIG. 4C, and FIG. 4D. Western blot of PKCδVIII and Bcl2 expression in (FIG. 4A) monocytic cell lines (THP-1) and (FIG. 4B) human neuronal (SH-SY5Y) incubated with G-CSF for 24 h (100 ng/mL or 200 ng/mL). Both PKCδVIII and Bcl2 expression are increased in the neuronal cells (100 ng/mL; 5.3 nM), and in the monocytic cells (200 ng/mL; 10.6 nM). The above graphs (FIG. 4C) and (FIG. 4D) show PKCδVIII or Bcl2 densitometric units normalized to GAPDH, (Bcl1 or PKCδVIII densitometric units÷GADPH densitometric units x 100) and represent three separate experiments. The results were analyzed with two-tailed Student's t-test; (*) indicates p<0.0001 comparing G-CSF treatment to corresponding untreated controls.
Figure 4B:
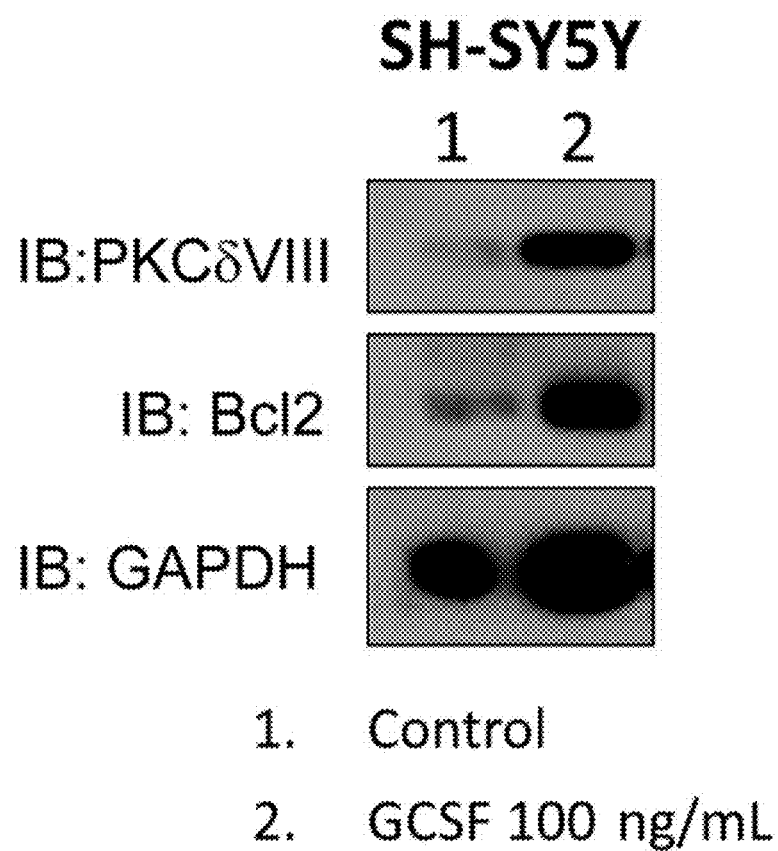
Figure 4C:
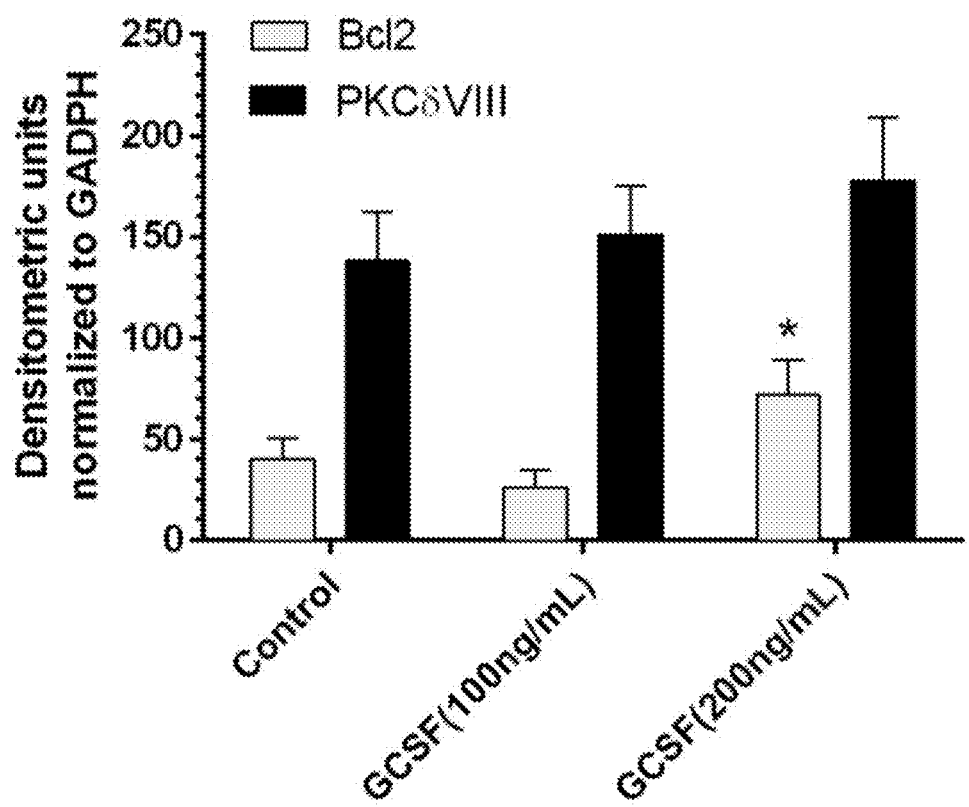
Figure 4D:
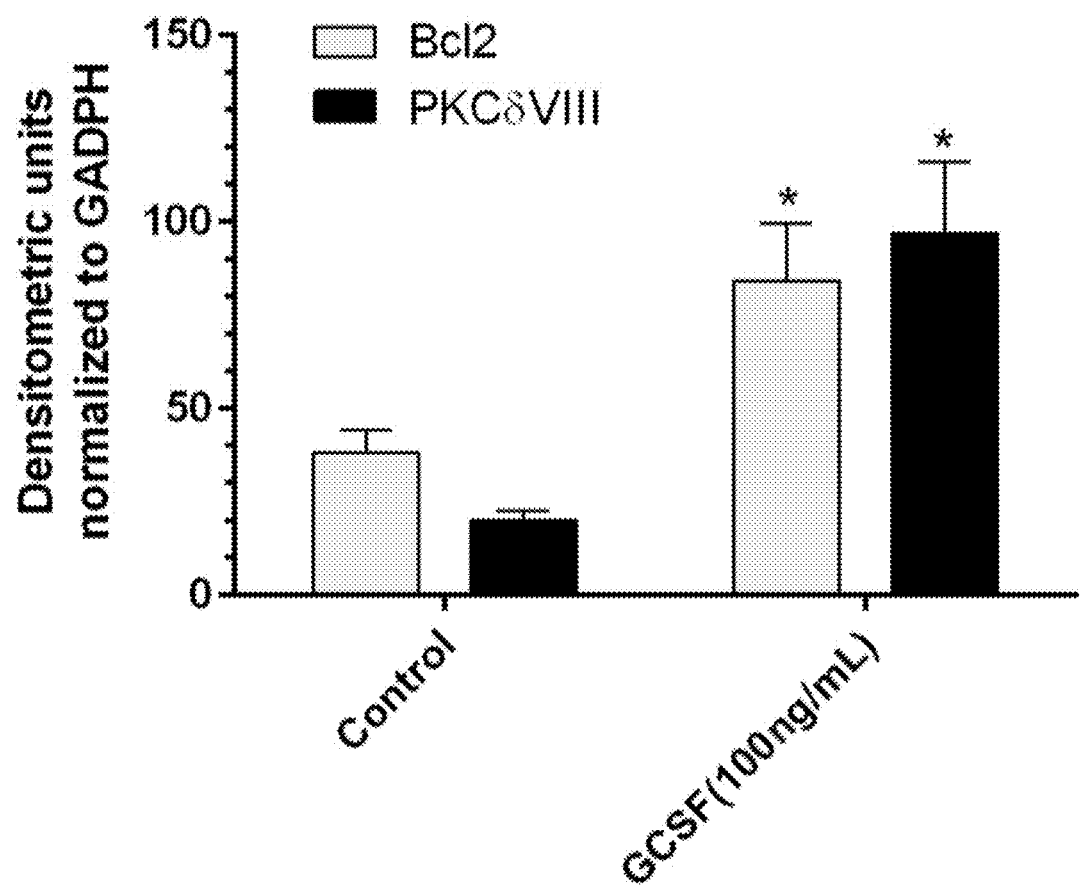

Described herein are compounds and their use in treating various disorders including neurodegenerative disorders. Using computer-assisted 3D molecular modeling and the crystal structure of granulocyte-colony stimulating factor receptor (G-CSF-R), small molecules were fit into the binding site(s) of the natural ligand for the G-CSF-R. A site and mechanism by which the protein/protein interaction can be blocked with small molecules was discovered. Several small molecule compounds were identified. These small molecules were used to investigate binding characteristics and the capacity to trigger intracellular signals similar to those activated by G-CSF. The compounds as disclosed herein may be agonists, antagonists, or partial agonists/antagonists of the G-CSF-R. The compounds as disclosed herein may be used, either alone or in combination with G-CSF, in methods of treating various disorders including neurodegenerative disorders. Effects elicited may include interacting or binding with the G-CSF receptor, triggering signal transduction, acting as a neurotrophic factor, stimulating neurons that bear G-CSF receptor, and blocking the peripheral effects of G-CSF to prevent excessive leukocytosis. The compounds described herein provide advantages over methods of administering G-CSF directly, as G-CSF is expensive to manufacture and costly to administer, the primary peripheral actions of G-CSF (such as to stimulate hematopoiesis and increase circulating levels of polymorphonucleocytes) limit the doses that can be used safely to treat brain disorders, and there are currently no known specific G-CSF receptor antagonists capable of blocking the peripheral actions of G-CSF, leaving intact the direct neurotrophic effects in the brain.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" or "alkoxyl" as used herein, refers to an alkyl group, as defined herein, appended to the parent molecular moiety through an oxygen atom. The term "$C_1$-$C_{12}$ alkoxy" means a $C_1$-$C_{12}$ alkyl group appended to the parent molecular moiety through an oxygen atom. The term "$C_1$-$C_4$ alkoxy" means a $C_1$-$C_4$ alkyl group appended to the parent molecular moiety through an oxygen atom. Representative examples of alkoxy include, but are not limited to, methoxy, ethoxy, propoxy, 2-propoxy, butoxy, and tert-butoxy.

The term "alkyl" as used herein, means a straight or branched, saturated hydrocarbon chain containing from 1 to 20 carbon atoms. The term "$C_1$-$C_{12}$ alkyl" means a straight or branched chain hydrocarbon containing from 1 to 12 carbon atoms. The term "lower alkyl" or "$C_1$-$C_4$ alkyl" means a straight or branched chain hydrocarbon containing from 1 to 4 carbon atoms. The term "$C_1$-$C_3$ alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means an unsaturated hydrocarbon chain containing from 2 to 20 carbon atoms and at least one carbon-carbon double bond.

The term "alkynyl" as used herein, means an unsaturated hydrocarbon chain containing from 2 to 20 carbon atoms and at least one carbon-carbon triple bond.

The term "alkoxyalkyl" as used herein, refers to an alkoxy group, as defined herein, appended to the parent molecular moiety through an alkylene group, as defined herein.

The term "arylalkyl" as used herein, refers to an aryl group, as defined herein, appended to the parent molecular moiety through an alkylene group, as defined herein.

The term "alkylene" as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aminoalkyl," as used herein, means at least one amino group, as defined herein, is appended to the parent molecular moiety through an alkylene group, as defined herein.

The term "amino" as used herein, means —NR$_x$R$_y$, wherein R$_x$ and R$_y$ may be hydrogen, alkyl, cycloalkyl, aryl, heteroaryl, heterocycle, alkenyl, or heteroalkyl. In the case of an aminoalkyl group or any other moiety where amino appends together two other moieties, amino may be —NR$_x$—, wherein R$_x$ may be hydrogen, alkyl, cycloalkyl, aryl, heteroaryl, heterocycle, alkenyl, or heteroalkyl. In some embodiments, amino is —NH$_2$.

The term "aryl" as used herein, refers to an aromatic group such as a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl, and tetrahydroquinolinyl.

The term "carboxyl" as used herein, means a carboxylic acid, or —COOH.

The term "cycloalkyl" means a monovalent saturated hydrocarbon ring or carbocyclic group. The term "cycloalkenyl" means a monovalent unsaturated hydrocarbon ring, and cycloalkenyl groups include at least one alkenyl. The term "cycloalkynyl" means a monovalent unsaturated hydrocarbon ring, and cycloalkynyl groups include at least one alkynyl. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. Cycloalkyl groups include, for example, cyclopropyl, cyclobutyl, cyclopentyl, cyclohexyl, cyclohexenyl, and cycloheptyl.

The term "haloalkyl" as used herein, means an alkyl group, as defined herein, in which one, two, three, four, five, six, seven, or eight hydrogen atoms are replaced by a halogen. Representative examples of haloalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "halogen" or "halo" as used herein, means Cl, Br, I, or F.

The term "heteroalkyl" as used herein, means an alkyl group, as defined herein, in which at least one of the carbons of the alkyl group is replaced with a heteroatom, such as oxygen, nitrogen, and sulfur. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system, including at least one heteroatom, such as N, O, and S. The aromatic monocyclic rings are five or six membered rings containing at least one heteroatom independently selected from the group consisting of N, O, and S. The five membered aromatic monocyclic rings have two double bonds, and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic" as used herein means a monocyclic heterocycle, a bicyclic heterocycle (heterobicyclic), or a tricyclic heterocycle. The monocyclic heterocycle is a three-, four-, five-, six-, seven-, or eight-membered ring containing at least one heteroatom independently selected from the group consisting of O, N, and S. Heterocycloalkyl groups include carbon-carbon bonds that are all single bonds, heterocycloalkenyl groups include at least one alkenyl, and heterocycloalkynyl groups include at least one alkynyl. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroarylalkyl" as used herein, refers to a heteroaryl group, as defined herein, appended to the parent molecular moiety through an alkylene group, as defined herein.

The term "heterocycloalkyl" as used herein, refers to a heterocycle group, as defined herein, appended to the parent molecular moiety through an alkylene group, as defined herein.

The term "hydroxyl" or "hydroxy" as used herein, means an —OH group.

The term "hydroxyalkyl" as used herein, means at least one —OH group, is appended to the parent molecular moiety through an alkylene group, as defined herein.

The term "nitro" means a —NO$_2$ group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$ alkyl" refers to an alkyl substituent containing from 1 to 3 carbon atoms.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "administration" or "administering," as used herein, refers to providing, contacting, and/or delivery of a compound or agent by any appropriate route to achieve the desired effect. These compounds or agents may be administered to a subject in numerous ways including, but not limited to, orally, ocularly, nasally, intravenously, topically, as aerosols, suppository, etc. and may be used in combination.

The term "agonist" refers to a biologically active ligand that binds to its complementary biologically active receptor and activates the receptor either to cause a biological response in the receptor or to enhance a biological activity of the receptor. An agonist may trigger (e.g., initiate or promote), partially or fully enhance, stimulate, or activate one or more biological activities. An agonist may mimic the action of a naturally occurring substance. An agonist of G-CSF-R induces the same intracellular biological response as those triggered by G-CSF.

The term "antagonist" means an agent that inhibits the effect of an agonist. The term "antagonist" may also refer to a molecule which blocks (e.g., reduces or prevents) a biological activity.

The terms "control," "reference level," and "reference" are used herein interchangeably. The reference level may be a predetermined value or range, which is employed as a benchmark against which to assess the measured result. "Control group" as used herein refers to a group of control subjects. The predetermined level may be a cutoff value from a control group. The predetermined level may be an average from a control group. Cutoff values (or predetermined cutoff values) may be determined by Adaptive Index Model (AIM) methodology. Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis is provided in P. J. Heagerty et al. (*Biometrics* 2000, 56, 337-44), the disclosure of which is hereby incorporated by reference in its entirety. Alternatively, cutoff values may be determined by a quartile analysis of biological samples of a patient group. For example, a cutoff value may be determined by selecting a value that corresponds to any value in the 25th-75th percentile range, preferably a value that corresponds to the 25th percentile, the 50th percentile or the 75th percentile, and more preferably the 75th percentile. Such statistical analyses may be performed using any method known in the art and can be implemented through any number of commercially available software packages (e.g., from Analyse-it Software Ltd., Leeds, UK; StataCorp LP, College Station, Tex.; SAS Institute Inc., Cary, N.C.). The healthy or normal levels or ranges for a target or for a protein activity may be defined in accordance with standard practice. A control may be a subject, or a sample therefrom, whose disease state is known. The subject, or sample therefrom, may be healthy, diseased, diseased prior to treatment, diseased during treatment, diseased after treatment, or healthy after treatment, or a combination thereof. The term "normal subject" as used herein means a healthy subject, i.e. a subject having no clinical signs or symptoms of disease. The normal subject is clinically evaluated for otherwise undetected signs or symptoms of disease, which evaluation may include routine physical examination and/or laboratory testing. In some embodiments, the control is a healthy control. In some embodiments, the control comprises neurodegenerative disease.

The term "effective dosage" or "therapeutic dosage" as used herein means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual.

The terms "inhibit" or "inhibiting" mean that an activity is decreased or prevented in the presence of an inhibitor as opposed to in the absence of the inhibitor. The term "inhibition" refers to the reduction or down regulation of a process or the elimination of a stimulus for a process, which results in the absence or minimization of the expression or activity of a biomarker or polypeptide. Inhibition may be direct or indirect. Inhibition may be specific, that is, the inhibitor inhibits a biomarker or polypeptide and not others.

"Neurodegenerative Diseases" are disorders characterized by, resulting from, or resulting in the progressive loss of structure or function of neurons, including death of neurons. Neurodegeneration can be found in many different levels of neuronal circuitry ranging from molecular to systemic. Some neurodegenerative diseases are caused by genetic mutations. Some neurodegenerative diseases are classified as proteopathies because they are associated with the aggregation of misfolded proteins. Neurodegenerative diseases include, for example, Alzheimer's Disease (AD), amyotrophic lateral sclerosis (ALS), Parkinson's Disease (PD), prion disease, motor neuron disease, Huntington's Disease, spinocerebellar ataxia, and spinal muscular atrophy.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three dimensional structure of a polypeptide monomer. "Quaternary structure" refers to the three dimensional structure formed by the noncovalent association of independent tertiary units.

"Recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed, or not expressed at all.

"Sample" or "test sample" as used herein can mean any sample in which the presence and/or level of a biomarker or target is to be detected or determined. Samples may include liquids, solutions, emulsions, mixtures, or suspensions. Samples may include a medical sample. Samples may include any biological fluid or tissue, such as blood, whole blood, fractions of blood such as plasma and serum, peripheral blood mononuclear cells (PBMCs), muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. Samples may be obtained before treatment, before diagnosis, during treatment, after treatment, or after diagnosis, or a combination thereof.

The term "specificity" as used herein refers to the number of true negatives divided by the number of true negatives plus the number of false positives, where specificity ("spec") may be within the range of $0<\text{spec}<1$. Hence, a method that has both sensitivity and specificity equaling one, or 100%, is preferred.

By "specifically binds," it is generally meant that a compound or polypeptide binds to a target when it binds to that target more readily than it would bind to a random, unrelated target.

"Subject" as used herein can mean a mammal that wants or is in need of the herein described compounds or methods. The subject may be a human or a non-human animal. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be of any age or stage of development, such as, for example, an adult, an adolescent, or an infant.

"Traumatic brain injury" or "TBI" refers to insult to the brain caused by an external physical force that may produce a diminished or altered state of consciousness and that results in an impairment of cognitive abilities or physical functioning. The pathology of TBI may include three phases: (1) primary injury to brain tissue and/or the cerebral vasculature; (2) the secondary injury, which includes physiological, neuroinflammatory, and biochemical processes triggered by the primary insult; and (3) regenerative responses, including enhanced proliferation of neural progenitor cells and endothelial cells. Brain regions include, for example, hippocampus, cortex, striatum, and corpus callosum.

The terms "treat," "treated," or "treating" as used herein refers to a therapeutic wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment.

"Variant" as used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indices of ±2 are substituted. The hydrophobicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof. In some embodiments, variants include homologues. Homologues may be polynucleotides or polypeptides or genes inherited in two species by a common ancestor.

2. Granulocyte Colony Stimulating Factor (G-CSF)

Granulocyte-colony stimulating factor (G-CSF or GCSF) is also known as colony-stimulating factor 3 (CSF 3). G-CSF is a glycoprotein that may act as a cytokine and/or hormone, as a type of colony-stimulating factor. G-CSF may be produced by a number of different tissues such as, for example, endothelium, macrophages, and other immune cells.

G-CSF may comprise a polypeptide of SEQ ID NO: 1. G-CSF polypeptide may be encoded by a polynucleotide of SEQ ID NO: 2. Commercially available forms of G-CSF include filgrastim and lenograstim. Commercially available filgrastim includes ZARXIO® (Novartis, Basel, Switzerland), GRANIX® (Teva Pharmaceuticals Industries Ltd., Petah Tikva, Israel), and NEUPOGEN® (Amgen Inc., Thousand Oaks, Calif.). Commercially available lenograstim includes GRANOCYTE™ (Chugai Pharmaceutical Co., Tokyo, Japan).

G-CSF binds the G-CSF receptor (G-CSF-R) to elicit its effects.

a. Granulocyte Colony Stimulating Factor Receptor (G-CSF-R)

Granulocyte-colony stimulating factor receptor (G-CSF-R) is a cell surface receptor and binds G-CSF. G-CSF-R may comprise a polypeptide of SEQ ID NO: 3. G-CSF-R may be found, for example, on the cell surface of precursor cells in the bone marrow, and on the cell surface of neurons in the brain and spinal cord. G-CSF-R may be found in the brain in the neurogenic zone of the hippocampus, the sub-ventricular zone, the olfactory bulb, pyramidal cells in corticol layers, entorhinal cortex, and/or Purkinje cells of the cerebellum. G-CSF-R may also be found on the surfaces of endothelial cells, lymphocytes, platelets, and/or neutrophils. In some embodiments, G-CSF-R is from human. In some embodiments, G-CSF-R is from mouse. G-CSF-R has a composite structure consisting of an immunoglobulin-like (Ig) domain, a cytokine-receptor homologous (CRH) domain, and three fibronectin type III (FNIII) domains in the extracellular region. The CRH region of G-CSF-R is a domain for ligand binding and for mediating the signal.

Binding of G-CSF to G-CSF-R triggers homodimerization of the receptor and activation of complex signal transduction and anti-apoptotic pathways. Upon binding G-CSF-R, the effects of G-CSF include peripheral and central activities. Central activities of G-CSF are those in the central nervous system (CNS), such as, for example, inducing neurogenesis to increase neuroplasticity and to counteract apoptosis, serving as a neurotrophic factor, promoting neuronal survival, stimulating neural stem cell and/or progenitor cell proliferation in, for example, the hippocampus. Peripheral activities of G-CSF are those beyond the CNS, such as, for example, stimulating or increasing hematopoiesis and increasing levels of polymorphonucleocytes, increasing blood stem cells, and increasing circulating monocytes. The beneficial effects of G-CSF in the treatment of diseases or conditions may result from its central activities in the brain, rather than its peripheral effects. Binding of G-CSF to G-CSF-R may stimulate the bone marrow to produce granulocytes and stem cells and release them into the bloodstream; stimulate the survival, proliferation, differentiation, and function of neutrophil precursors and mature neutrophils; increase proliferation of neural stem/progenitor cells; promote or increase neurogenesis (the generation of new neurons in the brain) or enhance survival of new neurons in, for example, the hippocampus; promote brain repair and improve cognitive performance after TBI; increase the generation of white blood cells; increase the generation of hematopoietic stem/progenitor cells; activate astrocytes and/or microglia; increase levels of neurotrophic factors such as glial cell line derived neurotrophic factor (GDNF) and/or brain derived neurotrophic factor (BDNF); increase the expression of PKCδ isoforms; increase the expression of STAT3; increase the expression of Bcl-2; and/or decrease the expression of Bax; or any combination thereof.

a. Protein Kinase C Delta VIII (PKCδVIII)

Protein Kinase C Delta (PKCδ) is a serine/threonine kinase mediating cellular growth, differentiation, and apoptosis. PKCδ is alternatively spliced to generate isoforms with distinct functions in apoptosis. Mouse PKCδ has two alternatively spliced variants—PKCδI and PKCδII—which have opposite functions in cell proliferation, differentiation, and apoptosis (mouse PKCδII promotes survival while mouse PKCδI promotes apoptosis). Mouse PKCδII is generated by utilization of an alternative downstream 5' splice site of PKCδ pre-mRNA exon 9. Mouse PKCδII is resistant to cleavage by caspase-3 and may be associated with and promote neurogenesis and neuronal differentiation. PKCδVIII is the human homolog of mouse PKCδII. Human PKCδVIII is an anti-apoptotic protein.

b. Signal Transducer and Activator of Transcription 3 (STAT3)

Signal transducer and activator of transcription 3 (STAT3) is a protein and transcription factor. In response to cytokines and growth factors, STAT3 is phosphorylated by receptor-associated Janus kinases (JAK), forms homo- or heterodimers, and translocates to the cell nucleus where it acts as a transcription factor. STAT3 mediates the expression of a variety of genes in response to cell stimuli and plays a key role in many cellular processes such as cell growth and apoptosis.

c. B-Cell Lymphoma 2 (Bcl2)

Upon binding G-CSF-R, G-CSF may act as a neurotrophic factor to upregulate the expression of Bcl2. Bcl2 is a protein localized to the outer membrane of mitochondria and inhibits apoptosis. Activation of the mitochondrial pathway of apoptosis culminates in mitochondrial outer membrane permeabilization and cell death. BAX and BAK are proteins that disrupt the mitochondrial membrane, and the antiapoptotic protein Bcl2 constrains or inhibits BAX and BAK.

d. Bax

BAX is a protein that regulates apoptosis and is also known as Bcl-2-like protein 4. BAX is found in the cytosol or associated with organelle membranes. BAX may interact with, and increase the opening of, the mitochondrial voltage-dependent anion channel (VDAC), which leads to the loss in membrane potential and the release of cytochrome c. Alternatively, BAX may help form an oligomeric pore in the mitochondrial membrane. The action of BAX on the mitochondrial membrane culminates in mitochondrial outer membrane permeabilization and cell death.

3. Compounds

Detailed herein are compounds that modulate the activity of G-CSF and/or G-CSF-R. The compound may be according to Formula I:

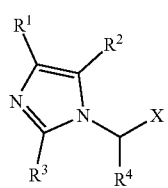

(I)

wherein $R^1$ and $R^2$ are each hydrogen, or $R^1$ and $R^2$ together with the carbon atoms to which they are attached form a phenyl ring;

$R^3$ and $R^4$ are each hydrogen, or $R^3$ and $R^4$ together with the atoms to which they are attached form a six-membered heterocyclic ring, wherein the ring is unsubstituted or substituted with one substituent selected from amino, nitro, methyl, ethyl, and hydroxyl;

X is —C($R^5$)($R^6$)-phenyl wherein the phenyl is substituted with $R^7$ and $R^8$, or X is indole substituted with 0, 1, 2, or 3 $R^9$, or X is pyrazole substituted with phenyl wherein the phenyl is substituted with 0, 1, 2, or 3 $R^{10}$;

$R^5$ and $R^6$ are each independently selected from hydrogen, hydroxyl, $C_1$-$C_4$ alkyl, $C_1$-$C_4$ alkoxy, or $R^5$ and $R^6$ together form an oxo group;

$R^7$ is hydrogen, hydroxyl, $C_1$-$C_{12}$ alkyl, or $C_1$-$C_{12}$ alkoxy;

$R^8$ is halogen, hydrogen, hydroxyl, $C_1$-$C_4$ alkyl, or $C_1$-$C_4$ alkoxy;

each $R^9$ is independently halogen, hydrogen, hydroxyl, $C_1$-$C_4$ alkyl, $C_1$-$C_4$ alkoxy, amino, or nitro; and each $R^{10}$ is independently halogen, hydrogen, hydroxyl, $C_1$-$C_4$ alkyl, $C_1$-$C_4$ alkoxy, amino, or nitro.

In some embodiments, $R^1$ and $R^2$ are each hydrogen. In some embodiments, $R^1$ and $R^2$ together with the carbon atoms to which they are attached form a phenyl ring.

In some embodiments, $R^3$ and $R^4$ are each hydrogen. In some embodiments, $R^3$ and $R^4$ together with the atoms to which they are attached form a six-membered heterocyclic ring, wherein the ring is unsubstituted or substituted with one substituent selected from amino, nitro, methyl, ethyl, or hydroxyl. In some embodiments, the six-membered heterocyclic ring is substituted with amino. In some embodiments, the six-membered heterocyclic ring is substituted with nitro.

In some embodiments, X is —C($R^5$)($R^6$)-phenyl wherein the phenyl is substituted with $R^7$ and $R^8$. In some embodiments, $R^5$ and $R^6$ are each independently hydroxyl or methyl. In some embodiments, $R^5$ and $R^6$ together form an oxo group. In some embodiments, $R^7$ is hydroxyl or alkoxy. In some embodiments, $R^7$ is hydroxyl. In some embodiments, $R^8$ is halogen. In some embodiments, $R^8$ is halogen, and halogen is Cl.

In some embodiments, X is indole substituted with one or two $R^9$. In some embodiments, each $R^9$ is independently halogen or methoxy.

In some embodiments, X is pyrazole substituted with phenyl wherein the phenyl is substituted with 0, 1, 2, or 3 $R^{10}$. In some embodiments, each $R^{10}$ is independently hydroxyl, methoxy, or nitro. In some embodiments, the phenyl is substituted with 0 or 1 $R^{10}$.

In some embodiments, the compound is of Formula I, wherein $R^1$ and $R^2$ are each hydrogen, $R^3$ and $R^4$ are each hydrogen, X is —C($R^5$)($R^6$)-phenyl wherein the phenyl is substituted with $R^7$ and $R^8$, wherein $R^5$ is hydroxyl, $R^6$ is methyl, $R^7$ is $C_7$ alkoxy, and $R^8$ is halogen.

In some embodiments, the compound is of Formula I, wherein $R^1$ and $R^2$ are each hydrogen, $R^3$ and $R^4$ are each hydrogen, X is —C($R^5$)($R^6$)-phenyl wherein the phenyl is substituted with $R^7$ and $R^8$, wherein $R^5$ is hydroxyl, $R^6$ is methyl, $R^7$ is $C_8$ alkoxy, and $R^8$ is halogen.

In some embodiments, the compound is of Formula I, wherein $R^1$ and $R^2$ are each hydrogen, $R^3$ and $R^4$ are each hydrogen, X is —C($R^5$)($R^6$)-phenyl wherein the phenyl is substituted with $R^7$ and $R^8$, wherein $R^5$ is hydroxyl, $R^6$ is methyl, $R^7$ is $C_9$ alkoxy, and $R^8$ is halogen.

In some embodiments, the compound is of Formula I, wherein $R^1$ and $R^2$ are each hydrogen, $R^3$ and $R^4$ are each hydrogen, X is —C($R^5$)($R^6$)-phenyl wherein the phenyl is substituted with $R^7$ and $R^8$, wherein $R^5$ is hydroxyl, $R^6$ is methyl, $R^7$ is hydroxyl, and $R^8$ is halogen.

In some embodiments, the compound is of Formula I, wherein $R^1$ and $R^2$ are each hydrogen, $R^3$ and $R^4$ are each hydrogen, X is —C($R^5$)($R^6$)-phenyl wherein the phenyl is substituted with $R^7$ and $R^8$, wherein $R^5$ and $R^6$ together form an oxo group, $R^7$ is hydroxyl, and $R^8$ is halogen.

In some embodiments, the compound is of Formula I, wherein $R^1$ and $R^2$ together with the carbon atoms to which they are attached form a phenyl ring, $R^3$ and $R^4$ together with the atoms to which they are attached form a six-membered heterocyclic ring wherein the ring is substituted with amino, and X is indole substituted with one $R^9$, wherein $R^9$ is halogen.

In some embodiments, the compound is of Formula I, wherein $R^1$ and $R^2$ together with the carbon atoms to which they are attached form a phenyl ring, $R^3$ and $R^4$ together with the atoms to which they are attached form a six-membered heterocyclic ring wherein the ring is substituted with amino, and X is indole substituted with one $R^9$, wherein $R^9$ is methoxy.

In some embodiments, the compound is of Formula I, wherein $R^1$ and $R^2$ together with the carbon atoms to which they are attached form a phenyl ring, $R^3$ and $R^4$ together with the atoms to which they are attached form a six-membered heterocyclic ring wherein the ring is substituted with amino, and X is pyrazole substituted with phenyl wherein the phenyl is substituted with one $R^{10}$, wherein $R^{10}$ is hydroxyl.

In some embodiments, the compound is of Formula I, wherein $R^1$ and $R^2$ together with the carbon atoms to which they are attached form a phenyl ring, $R^3$ and $R^4$ together with the atoms to which they are attached form a six-membered heterocyclic ring wherein the ring is substituted with amino, and X is pyrazole substituted with phenyl wherein the phenyl is substituted with one $R^{10}$, wherein $R^{10}$ is methoxy.

In some embodiments, the compound is of Formula I, wherein $R^1$ and $R^2$ together with the carbon atoms to which they are attached form a phenyl ring, $R^3$ and $R^4$ together with the atoms to which they are attached form a six-membered heterocyclic ring wherein the ring is substituted with amino, and X is pyrazole substituted with phenyl wherein the phenyl is substituted with one $R^{10}$, wherein $R^{10}$ is nitro.

In some embodiments, the compound is according to Formula II:

(II)

wherein X is indole substituted with 0, 1, 2, or 3 $R^9$, or X is pyrazole substituted with phenyl wherein the phenyl is substituted with 0, 1, 2, or 3 $R^{10}$;

each $R^9$ is independently halogen, hydrogen, hydroxyl, $C_1$-$C_4$ alkyl, $C_1$-$C_4$ alkoxy, amino, or nitro; and each $R^{10}$ is independently halogen, hydrogen, hydroxyl, $C_1$-$C_4$ alkyl, $C_1$-$C_4$ alkoxy, amino, or nitro.

In some embodiments, X is indole substituted with one $R^9$. In some embodiments, $R^9$ is halogen or methoxy.

In some embodiments, X is pyrazole substituted with phenyl, wherein the phenyl is substituted with one $R^{10}$. In some embodiments, $R^{10}$ is hydroxyl, methoxy, or nitro.

In some embodiments, the compound is of Formula II, wherein X is indole substituted with one $R^9$, wherein $R^9$ is halogen.

In some embodiments, the compound is of Formula II, wherein X is indole substituted with one $R^9$, wherein $R^9$ is methoxy.

In some embodiments, the compound is of Formula II, wherein X is pyrazole substituted with phenyl, wherein the phenyl is substituted with one $R^{10}$, wherein $R^{10}$ is hydroxyl.

In some embodiments, the compound is of Formula II, wherein X is pyrazole substituted with phenyl, wherein the phenyl is substituted with one $R^{10}$, wherein $R^{10}$ is methoxy.

In some embodiments, the compound is of Formula II, wherein X is pyrazole substituted with phenyl, wherein the phenyl is substituted with one $R^{10}$, wherein $R^{10}$ is nitro.

In some embodiments, the compound is according to Formula III:

(III)

wherein $R^5$ and $R^6$ are each independently hydrogen, hydroxyl, methyl, ethyl, methoxy, or ethoxy, or $R^5$ and $R^6$ together form an oxo group;

$R^7$ is hydrogen, hydroxyl, $C_1$-$C_{12}$ alkyl, or $C_1$-$C_{12}$ alkoxy; and $R^8$ is halogen, hydrogen, hydroxyl, $C_1$-$C_4$ alkyl, or $C_1$-$C_4$ alkoxy.

In some embodiments, $R^5$ and $R^6$ are each independently hydroxyl or methyl. In some embodiments, $R^5$ and $R^6$ together form an oxo group. In some embodiments, $R^7$ is hydroxyl or alkoxy. In some embodiments, $R^7$ is hydroxyl. In some embodiments, $R^8$ is halogen. In some embodiments, $R^8$ is halogen, and halogen is Cl.

In some embodiments, the compound is of Formula III, wherein $R^5$ is hydroxyl, $R^6$ is methyl, $R^7$ is $C_7$ alkoxy, and $R^8$ is halogen.

In some embodiments, the compound is of Formula III, wherein $R^5$ is hydroxyl, $R^6$ is methyl, $R^7$ is $C_8$ alkoxy, and $R^8$ is halogen.

In some embodiments, the compound is of Formula III, wherein $R^5$ is hydroxyl, $R^6$ is methyl, $R^7$ is $C_9$ alkoxy, and $R^8$ is halogen.

In some embodiments, the compound is of Formula III, wherein $R^5$ is hydroxyl, $R^6$ is methyl, $R^7$ is hydroxyl, and $R^8$ is halogen.

In some embodiments, the compound is of Formula III, wherein $R^5$ and $R^6$ together form an oxo group, $R^7$ is hydroxyl, and $R^8$ is halogen.

In some embodiments, the compound is selected from the following:

1

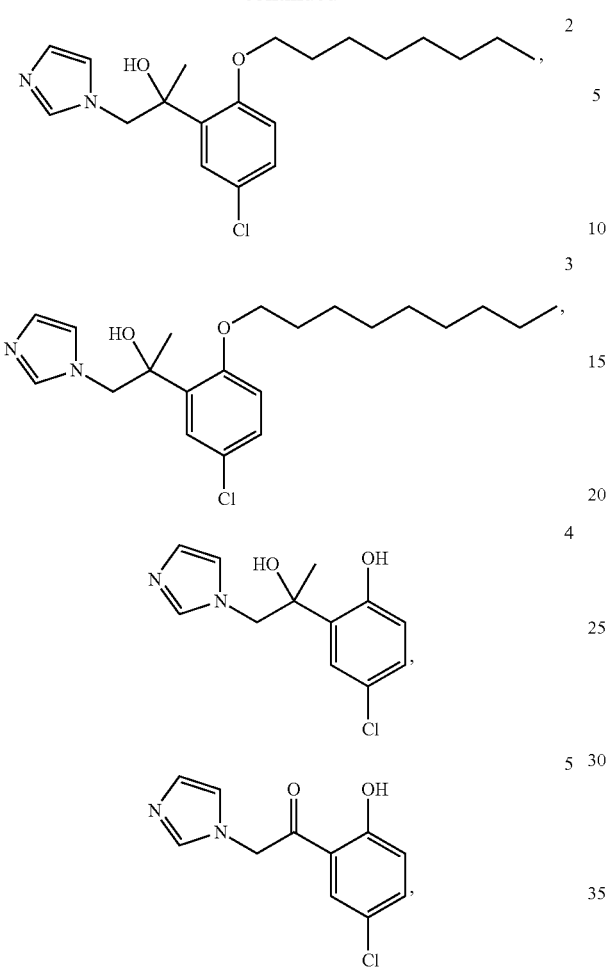
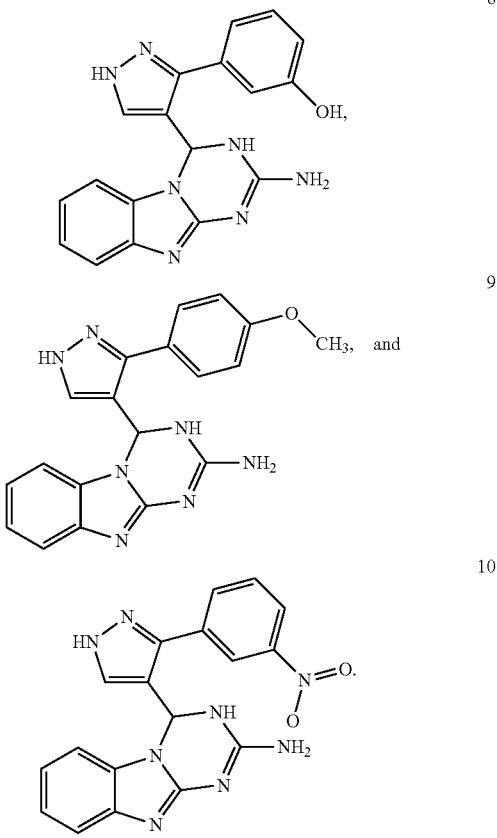
In some embodiments, the compound is selected from the following:

-continued
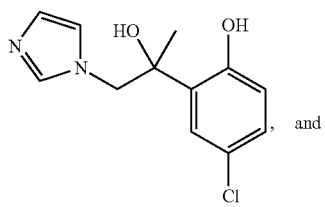
and
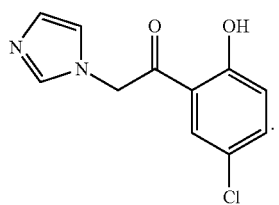
In some embodiments, the compound is selected from the following:
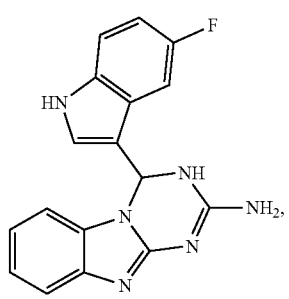
6
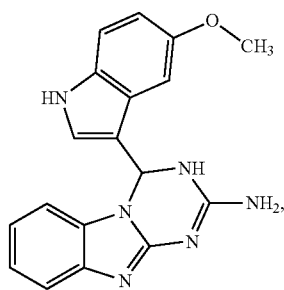
7
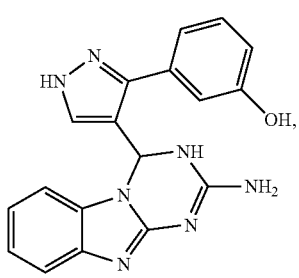
8
-continued
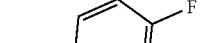
9
and
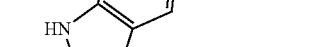
10
In some embodiments, the compound is selected from the following compounds:
6
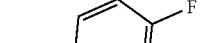
and
10
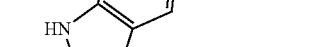
In some embodiments, the compound excludes or is not one of the following compounds:
1
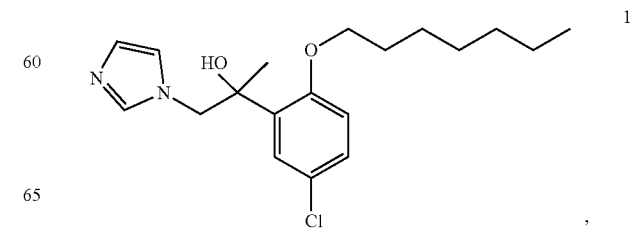

2

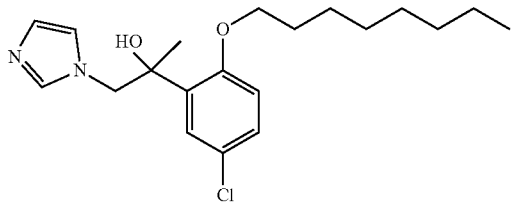

, and

3

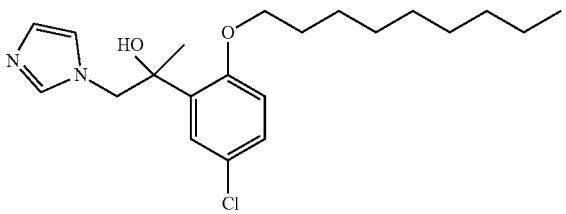

In some embodiments, the compound excludes or is not one of the following compounds:

6

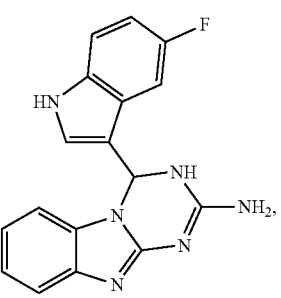

7

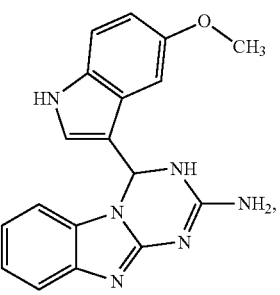

8

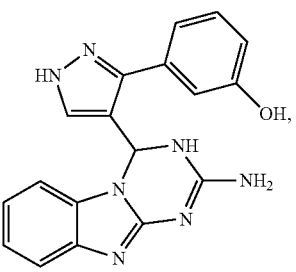

9

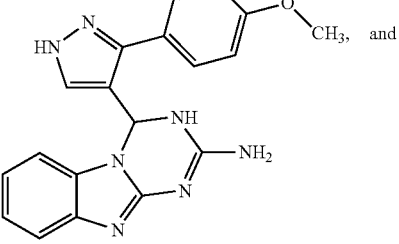

, and

10

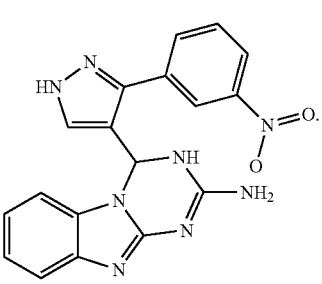

a. Synthesis of Compounds

Compounds 1-5 were obtained from Moffitt Cancer Center Chemistry unit (Tampa, Fla.). Alternatively, compounds 1-5 may be synthetically made by methods known to one of skill in the art. Compounds 6-10 are commercially available, for example, from Chembridge Corporation (San Diego, Calif.). Alternatively, compounds 6-10 may be synthetically made by methods known to one of skill in the art.

b. Effects of Compounds

The compounds as detailed herein may act as agonists, antagonists, or partial agonists/antagonists of G-CSF-R. In some embodiments, the compound modulates the effects of G-CSF-R. In some embodiments, the compound modulates the effects of G-CSF. In some embodiments, the compound binds G-CSF-R. In some embodiments, the compound binds G-CSF-R with greater affinity than G-CSF. In some embodiments, the compound binds G-CSF-R with less affinity than G-CSF. In some embodiments, the compound displaces G-CSF from G-CSF-R. The compound may displace at least 50%, at least 55%, at least 60%, at least 65%, at least 70%, at least 75%, at least 80%, at least 85%, at least 90%, or at least 95% of G-CSF from G-CSF-R. In some embodiments, the compound displaces at least 50% of G-CSF from the G-CSF receptor. In some embodiments, the compound displaces at least 75% of G-CSF from the G-CSF receptor.

In some embodiments, the compound is an agonist of G-CSF-R. The compound may trigger signal transduction pathways and effects similar to the effects of the natural ligand G-CSF, for example, those as detailed herein. The compound may mimic the neurotrophic and/or immune-modulating actions of G-CSF. In some embodiments, the compound is a central agonist of G-CSF-R. In such embodiments, the compound triggers effects similar to those of the natural ligand G-CSF in the CNS, but not those outside the CNS. In some embodiments, the compound is a peripheral agonist of G-CSF-R. In such embodiments, the compound triggers effects similar to those of the natural ligand G-CSF outside the central nervous system, but not those in the CNS.

The compound, upon administration to a subject, may elicit a variety of effects as an agonist of G-CSF-R. In some embodiments, the compound decreases amyloid burden, enhances neurogenesis, enhances synaptogenesis, enhances cognitive performance, increases expression of Bcl2, increases expression of PKCδVIII, increases expression of STAT3, decreases expression of Bax, or any combination thereof. In some embodiments, the compound increases expression of Bcl2. In some embodiments, the compound increases expression of PKCδVIII. In some embodiments, the compound increases expression of STAT3. In some embodiments, the compound decreases expression of Bax.

In some embodiments, the compound is a central antagonist of G-CSF-R. In such embodiments, the compound inhibits, or does not trigger, effects similar to those of the natural ligand G-CSF in the CNS, but has little to no activity outside the CNS. In some embodiments, the compound is a peripheral antagonist of G-CSF-R. In such embodiments, the compound inhibits, or does not trigger, effects similar to those of the natural ligand G-CSF outside the CNS, but has little to no activity in the CNS. In some embodiments, the compound has a minimal effect on leukopoiesis.

In some embodiments, the compound may act as a partial or mixed agonist/antagonist of G-CSF-R. In such embodiments, the compound elicits a combination of the agonist and antagonist effects detailed above. For example, the compound may be an antagonist of G-CSF biological responses in monocytes, but not neurons. The compound may be a central agonist and a peripheral antagonist.

The activity of the compound may be examined by measuring the capacity of the compound to displace labelled G-CSF from G-CSF-R expressed in cell lines. Suitable labels are known in the art, such as, for example, radiolabels. The cell line may include, for example, THP-1 (which is a human monocyte cell line representative of the peripheral immune system), and SH-SY5Y (which is a human neuroblastoma cell line). The compounds as detailed herein may displace labelled G-CSF from G-CSF-R expressed in cell lines.

The activity of the compound may be examined by measuring the expression of, for example, Bcl2 and/or PKCδVIII protein, in a cell line. The cell line may include, for example, THP-1 or SH-SY5Y. Bcl2 and/or PKCδVIII protein may be measured by a method according to one of skill in the art, such as, for example, immunoassays, Western blot, and probes to mRNA.

The activity of the compound may be examined by administering the compound to mice before, concomitantly, or after administering controlled corticol impact (CCI, an experimental TBI) to the mice, and then testing the mice in assays such as radial arm water maze (RAWM; a hippocampal-dependent spatial learning task that does not rely on locomotor ability or swimming speed), testing motor balance and coordination on a rotating cylinder (rotarod), measuring microglial and astroglial response, measuring hippocampal neurogenesis, measuring neurotropic factors such as brain-derived neurotrophic factor (BDNF) and glial cell line-derived neurotrophic factor (GDNF), and/or measuring cytokines in brain homogenates. Brain regions include, for example, hippocampus, cortex, striatum, and corpus callosum. The neurotropic factors and cytokines may be measured by any means known in the art such as, for example, immunohistochemistry. Astroglial and microglial response may be monitored by any means known in the art such as, for example, immunostaining with antibodies to GFAP and Iba-1, respectively. Neurogenesis may be measured, for example, by measuring the expression of doublecortin (DCX; a microtubule-associated protein and a marker of immature neurons) using an antibody to DCX. The central action of the compound in the CNS may be examined by comparing the effects of the compound with and without the presence of a selective chemokine receptor antagonist of monocyte chemoattractant protein-1 (MCP-1). In such embodiments, an MCP-1 inhibitor may be used to decrease the infiltration of bone marrow-derived cells (BMDC) such as monocytes into the CNS, to facilitate isolation of the peripheral action of recruiting monocytes from the blood into the brain from the central actions in the CNS. MCP-1 mediates recruitment of inflammatory cells to sites of tissue injury. Selective MCP-1 inhibitors include, for example, C—C motif receptor 2 (CCR2) antagonists. CCR2 is a G-protein-coupled receptor that binds its ligand MCP-1. CCR2 antagonists include, for example, RS504393 (6-methyl-10-[2-(5-methyl-2-phenyl-4-oxazolyl)ethyl]-spiro[4H-3,1-benzoxazine-4,40-piperidin]-2(1H)-one), which may be purchased commercially from, for example, Tocris Biosci Inc. (Minneapolis, Minn.). In some embodiments, the compound improves recovery in mice after CCI. In some embodiments, the direct actions of the compound in the CNS improve recovery in mice after CCI. In some embodiments, the compound improves motor function, such as, for example, after injury. In some embodiments, the compound improves spatial learning, such as, for example, after injury. In some embodiments, the compound improves performance in RAWM and/or rotarod after CCI. In some embodiments, the compound activates astrocytes and/or microglia. In some embodiments, the compound increases levels of GDNF and/or BDNF. In some embodiments, the compound increases expression of DCX and/or increases the number of cells expressing DCX. In some embodiments, the compound increases expression of GFAP. In some embodiments, the compound increases expression of Iba-1.

In some embodiments, the compound is co-administered with a G-CSF polypeptide, or in some embodiments, a polynucleotide encoding a G-CSF polypeptide.

In some embodiments, the compound treats disorders including, but not limited to, neurodegenerative disease, stroke, traumatic brain injury (TBI), impaired motor function, and impaired cognitive function, or any combination thereof.

4. Administration

A composition may comprise the compound detailed above. The compounds can be formulated into a composition in accordance with standard techniques well known to those skilled in the pharmaceutical art. The composition may be prepared for administration to a subject. Such compositions can be administered in dosages and by techniques well known to those skilled in the medical arts taking into consideration such factors as the age, sex, weight, and condition of the particular subject, and the route of administration.

The compound can be administered prophylactically or therapeutically. In prophylactic administration, the compound can be administered in an amount sufficient to induce a response. In therapeutic applications, the compounds are administered to a subject in need thereof in an amount sufficient to elicit a therapeutic effect. An amount adequate to accomplish this is defined as "therapeutically effective dose." Amounts effective for this use will depend on, e.g., the particular composition of the compound regimen administered, the manner of administration, the stage and severity of the disease, the general state of health of the patient, and the judgment of the prescribing physician.

The compound can be administered by methods well known in the art as described in Donnelly et al. (*Ann. Rev. Immunol.* 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The compound can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The compound can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the compound is administered intravenously, intraarterially, or intraperitoneally to the subject.

The compound can be a liquid preparation such as a suspension, syrup, or elixir. The compound can be incorporated into liposomes, microspheres, or other polymer matrices (such as by a method described in Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The compound may be used as a vaccine. The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation can be carried out via a minimally invasive device.

In some embodiments, the compound is administered in a controlled release formulation. The compound may be released into the circulation, for example. In some embodiments, the compound may be released over a period of at least about 1 day, at least about 2 days, at least about 3 days, at least about 4 days, at least about 5 days, at least about 6 days, at least about 7 days, at least about 1 week, at least about 1.5 weeks, at least about 2 weeks, at least about 2.5 weeks, at least about 3.5 weeks, at least about 4 weeks, or at least about 1 month.

5. Methods a. Methods of Treating a Condition

Provided herein are methods of treating a condition in a subject. The method may include administering to a subject a compound as detailed herein. In some embodiments, the condition is selected from the group consisting of neurodegenerative disease, stroke, traumatic brain injury (TBI), impaired motor function, and impaired cognitive function. In some embodiments, the neurodegenerative disease is selected from the group consisting of Alzheimer's Disease (AD), amyotrophic lateral sclerosis (ALS), Parkinson's Disease (PD), prion disease, motor neuron disease, Huntington's Disease, spinocerebellar ataxia, and spinal muscular atrophy.

b. Methods of Stimulating the Central Nervous System G-CSF-R

Provided herein are methods of stimulating the central nervous system G-CSF-R. The method may include administering to a subject a compound as detailed herein.

6. Examples

EXAMPLES

Example 1

Materials and Methods

Cell Cultures. Two human cell lines were chosen for cell culture studies. One was a human monocyte cell line that is representative of the peripheral immune system, THP-1, which grows in suspension. The other cell line was a human neuroblastoma cell line (SH-SY5Y) which is a mixed cell line although only adherent cells were utilized (Xie, H. R., et al. Chin. Med. J. (Engl) 2010, 123, 1086-92). Both cell lines are known to express the G-CSF-R. Both cell lines were purchased from ATCC (Manassas, Va.). THP-1 cells were cultured in RPMI-1640 medium supplemented with 10% fetal bovine serum (FBS) plus 1% penicillin-streptomycin (ATCC, Manassas, Va.) in a humidified atmosphere of 5% $CO_2$ at 37° C. SH-SY5Y cell line were cultured in 1:1 EMEM/F12 medium with 10% FBS plus 1% penicillin/streptomycin in a humidified atmosphere of 5% $CO_2$ at 37° C.

In Silico Modeling of G-CSF Receptor to Identify Potential G-CSF Mimetics or Antagonists. Compounds 1-3 (TABLE 1) were originally discovered by Kusano et al. (Blood 2004, 103, 836-42) and found to stimulate blood stem cell proliferation and to increase levels of circulating leukocytes in a rodent model. The other drugs were discovered using an initial screen based on in silico modeling of the G-CSF receptor (GCSF-R). Schödinger 3D-modeling software (https://www.schrodinger.com/smdd/) was used to import a molecular model of G-CSF bound to its receptor from the NCBI protein database (http://www.ncbi.nlm.nih.gov/protein/1PGR_C). G-CSF-R has previously been cloned, purified, and crystallized to generate X-ray diffraction patterns to allow reconstruction and visualization in 3D computer models. G-CSF-R has a composite structure consisting of an immunoglobulin-like (Ig) domain, a cytokine-receptor homologous (CRH) domain, and three fibronectin type III (FNIII) domains in the extracellular region. The CRH region of G-CSF-R is an essential domain for ligand binding and mediating the signal. G-CSF-R dimerization induced by G-CSF binding has been demonstrated to be a common signal transduction mechanism.

The goal in the modeling study was to find small molecules that fit the site(s) on the G-CSF-R where binding with its natural ligand G-CSF occurs. After modeling the first 3 molecules identified as potential G-CSF mimetics, other molecules were screened and selected for further study as potential inhibitors of the protein/protein interaction between G-CSF at its receptor site. Another objective was to test the capacity of these drugs to facilitate dimerization of the G-CSF-R to reproduce central and/or peripheral actions of G-CSF, i.e., to serve as G-CSF mimetic drugs.

Drugs. Ten compounds were utilized for the present study, as shown in TABLE 1.

TABLE 1

Chemical Names of Compounds Tested.

| | |
|---|---|
| 1 | 2-(5-chloro-2-heptyloxy)phenyl)-1-(1H-imidazol-1-yl)propan-2-ol |
| 2 | 2-(5-chloro-2-(octyloxy)phenyl)-1-(1H-imidazol-1-yl)propan-2-ol |

TABLE 1-continued

Chemical Names of Compounds Tested.

| | |
|---|---|
| 3 | 2-(5-chloro-2-(nonyloxy)phenyl)-1-(1H-imidazol-1-yl)propan-2-ol |
| 4 | 1-(5-chloro-2-hydroxyphenyl)-2-(1H-imidazol-1-yl)ethan-1-one |
| 5 | 1-(5-chloro-2-hydroxyphenyl)-2-(1H-imidazol-1-yl)ethan-1-one |
| 6 | 4-(5-methoxy-1H-indol-3-yl)-3,4-dihydro-[1,3,5]-triazino-[1,2a]benzimidazol-2-amine |
| 7 | 3-[4-(2-amino-3,4-dihydro-[1,3,5]triazino[1,2-a]benzimidazol-4-yl)-1H-pyrazol-3-yl]phenol |
| 8 | 4-[3-(4-methoxyphenyl)-1H-pyrazol-4-yl]-3,4-dihydro[1,3,5]triazino[1,2-a]benzimidazol-2-amine |
| 9 | 4-(5-fluoro-1H-indol-3-yl)-3,4-dihydro-[1,3,5]triazino[1,2-a]benzimidazol-2-amine |
| 10 | 4-[3-(3-nitrophenyl)-1H-pyrazol-4-yl]-3,4-dihydro[1,3,5]triazino[1,2-a]-benzimidazol-2-amine |

G-CSF Receptor Binding Parameters Assessed with [$^{125}$I]-G-CSF. Binding of [$^{125}$I]-G-CSF was measured using previously described method (Kondo, S., et al. *Eur. J. Haematol.* 1991, 46, 223-30) with some modifications (Pennington, A., et al. *Alzheimer's Disease and Parkinsonism* 2013, 3, 121). [$^{125}$I]-G-CSF (specific activity 46.55 TBq/mmol) was purchased from Perkin Elmer (Waltham, Mass.). Cells were incubated in 180 µL of binding medium containing 0.2% BSA, 5 mM MgSO$_4$, and 50 mM Hepes, pH 7.2 at a concentration of $1.5 \times 10^7$ cells/mL and the appropriate concentration of [$^{125}$I]-G-CSF. Incubations were carried out at room temperature with periodic shaking to ensure continuous mixing of cells and radioactive ligand. The incubation time of 2 h was estimated from preliminary experiments as being found sufficient to reach equilibrium. Nonspecific binding of [$^{125}$I]-G-CSF was measured by incubations in the presence of a 100-fold molar excess of unlabeled G-CSF. At the end of the incubation, bound and free radio ligands were discriminated by using separating oil according to previously published method (Dower, S. K., et al. *J. Exp. Med.* 1985, 162, 501-15). Namely, 80 µL aliquots were sampled from the incubation mixture, each aliquot was layered on 300 µL of separating oil placed in 500 µL polyethylene tubes and centrifuged for 5 min at 6000 rpm. The separating oil consisted of 1.5 parts dibutyl phthalate and 1 part bis(2-ethylhexyl)phthalate (Aldrich-Sigma, St. Louis, Mo.). Bound and free ligand activities were counted after cutting tubes in two pieces and placing the tips and tops, respectively into separate scintillation vials. Counting was performed on Beckman Coulter LS6500 scintillation counter. Glacial acetic acid was employed to solubilize the pellet. The specific binding was determined from the amount of bound [$^{125}$I]-G-CSF blocked by competition with excess unlabeled G-CSF. The parameters of saturation binding experiments including dissociation constant (Kd), maximum binding capacity (Bmax) and binding cooperativity (h) were calculated with GraphPad Prism 5 software (La Jolla, Calif.) by using nonlinear regression analysis.

Competition Studies. Cells, prepared as described above, were incubated in 180 µL of binding medium containing 0.2% BSA, 5 mM MgSO$_4$ and 50 mM Hepes, pH 7.2 at a concentration of $1.5 \times 10^7$ cells/mL and the appropriate concentration of [$^{125}$I]-G-CSF. This was followed by addition of increasing concentrations of each study compound (10 to 3000 nM). After 2 hrs of incubation, the amount of bound and free [$^{125}$I]-G-CSF was determined, as described above. From these data, the parameters of competition for the receptor were calculated with GraphPad Prism 5 software (La Jolla, Calif.). Each concentration was analyzed in triplicate and experiments were repeated three times. These experiments were conducted in human monocytic and neuronal cell lines.

Signal transduction triggered by G-CSF (measurement of PKCVlIII and Bcl2 with Western blot). THP-1 cells or SH-SY5Y cells $3 \times 10^6$ cells in 5 mL media in a 25 cm$^2$ flask were treated with 100 ng/mL G-CSF or three different concentrations of the test drug for 24 h. In addition, a set of flasks were co-incubated with the combination of G-CSF and 3 concentrations of test drug. Whole cell lysates (60 mg) were separated on 10% polyacrylamide gel electrophoresis-SDS (PAGE-SDS). Proteins were electrophoretically transferred to nitrocellulose membranes, blocked with 5% nonfat milk prepared on Tris buffered saline containing 0.1% Tween 20, washed and incubated with a polyclonal antibody against either Bcl2 (Cell Signaling, Danvers, Mass.) or PKCδVIII-specific polyclonal antibody (Jiang, K., et al. *Biochemistry* 2008, 47, 787-797). The house keeping gene GAPDH was used as an internal standard. Following incubation with anti-rabbit IgG-HRP, enhanced chemiluminesence (Pierce™, Thermo Scientific, Walthahm, Mass.) was used for detection and the gels were analyzed using UN-SCAN-IT™ software (Silk Scientific, Inc., Orem, Utah).

Radial Arm Water Maze (RAWM). To study the cognitive effects of G-CSF in mice that had undergone mild to moderate controlled cortical impact (CCI), a RAWM task will be employed. RAWM is a hippocampal-dependent, spatial learning task that does not rely on locomotor ability or swimming speed (Vorhees and Williams, *Nat. Protoc.* 2006, 1, 848-858). Baseline RAWM is conducted in all mice before CCR and repeated at day 7 and day 14 post-CCI. A six-arm radial arm maze was placed into a water tank of approximately 100-cm diameter and 25-cm height; a 5-cm-diameter platform was used. The platform was submerged 0.5 cm below the water surface, and the temperature of the water was kept at 268° C. Mice were placed in the start arm at the beginning of every trial, and the platform was located in the goal arm. Every animal had an assigned platform/arm location throughout acquisition of learning, yet the starting zone was randomly changed per trial. A spatial training protocol was followed. Mice were given two blocks of five trials, each. Based on prior experience the number of animals in each study was determined by establishing necessary group sizes to reach statistical significance for behavior and histological analysis in each study (Song, S., et al. *J. Neurosci. Res.* 2016, 94, 409-23; Song, S., et al., Restor. Neurol. *Neurosci.* 2016). A power calculation based on number of errors was made in finding the platform in the RAWM by untreated Tg mice and NT mice was made using experimental data. An n=8 for each group of mice (Tg and NT) had a 90% power to detect a difference between means of 1.12 errors with a significance level (alpha) of 0.05 (two-tailed).

Surgery and Controlled Cortical Impact (CCI). Animals will undergo TBI using a controlled cortical impactor (Pittsburgh Precision Instruments, Inc, USA) using methods we have previously described (Song, S., et al. *J. Neurosci. Res.* 2016, 94, 409-23; Song, S., et al., *Restor. Neurol. Neurosci.* 2016). Briefly, animals will initially receive Buprenorphine (0.05 mg/kg, s.c.) at the time of anesthesia induction (with gasesous anesthesia). Once deep anesthesia is achieved (by checking for pain reflexes), individual animals are fixed in a stereotaxic frame (David Kopf Instruments, Tujunga, Calif., USA). After exposing the skull, craniectomy (approximately 2 mm), to accommodate the impactor tip) is performed over the right frontoparietal cortex (−0.5 mm anteroposterior and +0.5 mm mediolateral to bregma). The pneumatically operated TBI device (with a convex tip diameter=2 mm) impacts the brain at a velocity of 6.0 m/s reaching a depth of 0.5 mm, 1.0 mm or 2.0 mm for mild, moderate and severe TBI respectively, below the dura mater layer and remains in the brain for 150 ms. The impactor rod is angled 15° to the vertical to maintain a perpendicular position in reference to the tangential plane of the brain curvature at the impact surface. A linear variable displacement transducer (Macrosensors, Pennsauken, N.J.), connected to the impactor, measures velocity and duration to verify consistency. Bone wax is used to cover the craniectomized region and the skin incision sutured thereafter. Sham injury surgeries consist of animals exposed to anesthesia, scalp incision, craniectomy, and suturing. A computer operated thermal blanket pad and a rectal thermometer allowed maintenance of body temperature within normal limits. All animals are closely monitored until recovery from anesthesia and over the next 3 consecutive days.

Immunohistology and quantitative image analyses. Mice were anesthetized with 150 mg/kg ketamine and 15 mg/kg xylazine and then transcardially perfused with 0.9% saline, followed by 4% paraformaldehyde. Brains were stored in 4% paraformaldehyde and were transferred to 25% sucrose solution in 4% paraformaldehyde until they sank to the bottom. Then, brains were slowly immersed in isopentane (cooled on dry ice), left in isopentane for 20 sec, removed, placed on a small piece of aluminum foil resting on powdered dry ice for 1-2 min (to allow the isopentane evaporate), and finally wrapped in the foil and stored at −80° C. until sectioning. Brains slices were cut 30 mL thick on a cryostat (Leica) set to 225° C. Every sixth coronal section was taken from the corpus striatum (caudate/putamen) spanning 1.2 mm in the anterior-posterior direction (from Bregma+1.32 mm to Bregma=0, which corresponds to the beginning of the lateral ventricles to the anterior commissure). Serial sections were also cut from the hippocampus, starting from Bregma −1.28 to Bregma −2.92. Every sixth section was kept for immunostaining. Selective immunostaining of astrocytes and microglia was performed with antibodies to GFAP and Iba-1, respectively. Iba-1 is protein that is specifically expressed in macrophages/microglia and is upregulated during the activation of these cells. Brain sections were preincubated in phosphate-buffered saline (PBS) containing 10% normal serum (goat or donkey; Vector Laboratories, Burlingame, Calif.) and 0.3% Triton X-100 (Sigma, St. Louis, Mo.) for 30 min. The sections were then transferred to a solution containing primary antibodies in 1% normal serum and 0.3% Triton X-100/PBS and incubated overnight at 4° C.

Estimates of Hippocampal Neurogenesis. Cells in hippocampus that are double-labeled with BrdU/nestin, BrdU/DCX, or BrdU/NeuN will be counted to determine extent of neurogenesis. Labeled cells will be visualized with fluorescence microscopy using appropriate filters or with Zeiss LSM 510 confocal fluorescence microscope. Unbiased estimates of the number of doubly labeled BrdU+ cells in dentate gyrus is made by counting in serially sectioned hippocampus according to the method previously described (Shors, T. J., et al. *Nature* 2001, 410, 372-376; Shors T. J., et al. *Hippocampus* 2002, 12, 578-584). Briefly, cell counts are estimated based on sectioning and counting positively labeled cells in every 6th section (30 μm thick) of tissue (180 μm). A modification to the optical dissector method was used so that cells on the upper and lower planes were not counted to avoid counting partial cells. The number of BrdU+ cells counted in every 6th section was multiplied by 6 to get the total number of BrdU+ cells in the dentate gyrus. For the quantification of double labeled cells using immunofluroescence, the number of BrdU+ and BrdU+NeuN+ labeled cells is estimated using every 12th section taken throughout the dentate gyrus. Positive labeling is verified by confocal microscopy (Zeiss LSM510). Cells determined to be BrdU+ and BrdU+NeuN+ positive are tallied and multiplied by the number of intervening sections.

The specific antibodies used will be rabbit anti-lba-1 (1:500; catalog No. 019-19741; RRID:nlx_152487; Wako, Osaka, Japan), rabbit anti-GFAP (1:50 in PBS; catalog No. 60-0032-7; RRID:AB_11203520; Genemed, San Francisco, Calif.), and rabbit anti-DCX (1:1,000 containing 1:100 normal serum without Triton X-100; catalog No. 18723; RRID:nlx_152244; Abcam, Cambridge, Mass.). After incubation with primary antibody, sections are washed and incubated for 1 hour with Alexa Fluor 488 goat anti-rabbit IgG diluted 1:400 in PBS (catalog No. A11070; RRID: AB_142134; Molecular Probes/Invitrogen, Carlsbad, Calif.) at room temperature. Sections were then rinsed in PBS three times and covered with a coverglass. Green fluorescence signals from the labeled cells are visualized by fluorescence microscopy with appropriate filters. For quantitative image analyses, all images will be acquired using an Olympus BX60 microscope with an attached digital camera system (DP-70, Olympus, Tokyo, Japan), and the digital image will be routed into a Windows PC for quantitative analysis using ImageJ (NIH). To evaluate microglial burden (Ibal immunoreactivity), after the mode of all images is converted to gray scale, the average intensity of positive signals from each image will be quantified in the CA1 and CA3 regions of hippocampus as a relative number from zero (white) to 255 (black). Each analysis is done by a single examiner blinded to sample identities.

Figure 7:
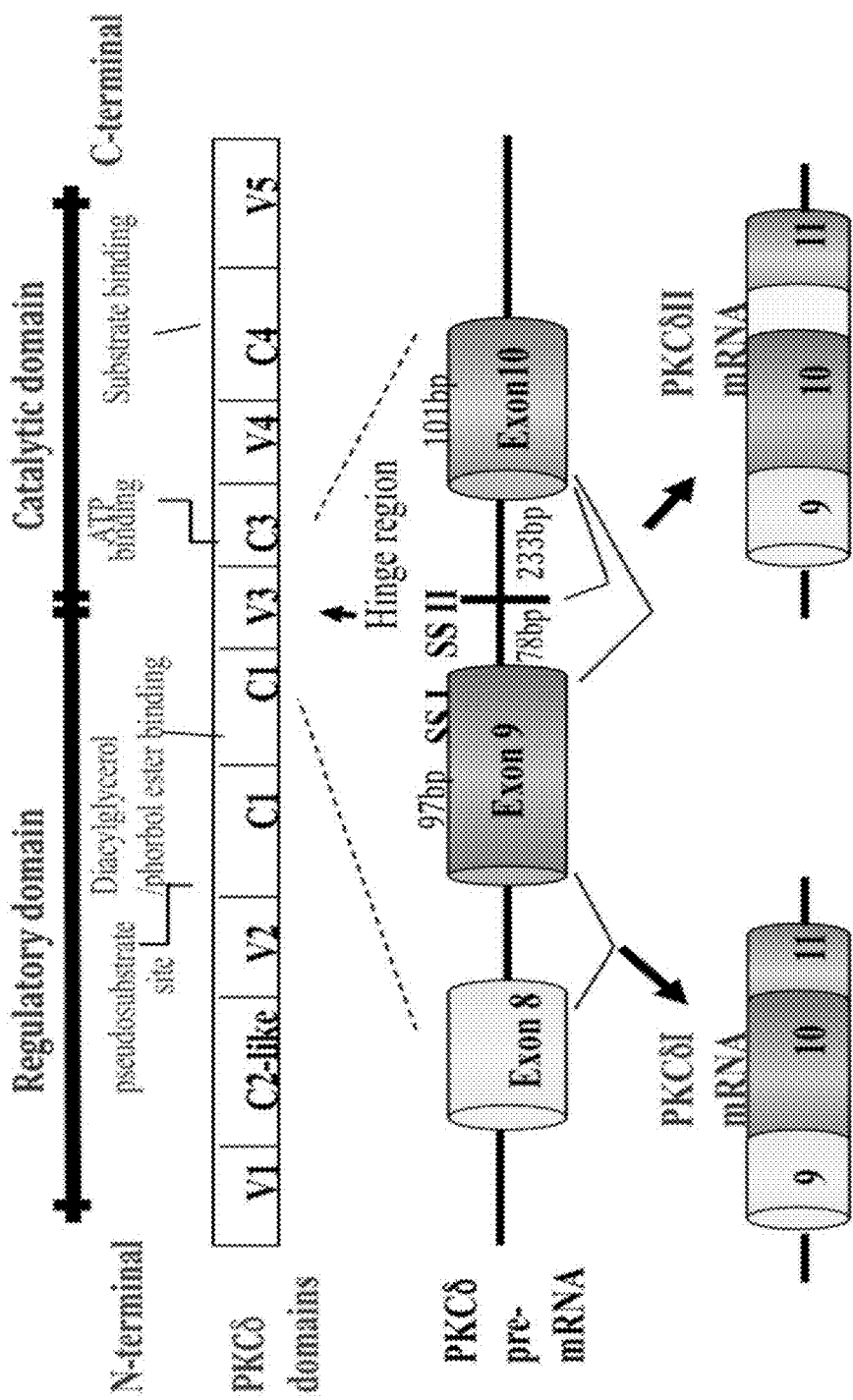
FIG. 7. Schematic of PKCδ domains and alternative splicing of pre-mRNA which generates the splice variants PKCδI and PKCδII in mice.

Intracellular signaling studies. The experiments will be performed using methods previously published from the Patel lab (Apostolatos, H., et al. *J. Biol. Chem.* 2010, 285, 25987-25995; Patel, N. A., et al. *Gene Expression* 2006, 13, 73-84). Briefly, the mouse splice variant PKCδII is generated by utilization of an alternative downstream 5' splice site of PKCδ pre-mRNA exon 9 (FIG. 7). PKCδII is resistant to cleavage by caspase-3. PKCδII promotes survival while PKCδI promotes apoptosis. PKCδVIII is the human homolog of PKCδII, and both splice variants promote survival. For quantitative image analyses, all images will be acquired using an Olympus BX60 microscope with an attached digital camera system (DP-70, Olympus, Tokyo, Japan), and the digital image will be routed into a Windows PC for quantitative analysis using ImageJ (NIH). To evaluate microglial burden (Ibal immunoreactivity), after the mode of all images is converted to gray scale, the average intensity of positive signals from each image will be quantified in the CA1 and CA3 regions of hippocampus as a relative number from zero (white) to 255 (black). Each analysis is done by a single examiner blinded to sample identities.

Signal transduction data analysis. This study elucidates a novel aspect of G-CSF signaling in the brain. The role of Akt kinase in the cell is complex as it can activate multiple cascades thereby regulating proteins involved in transcription and translation. G-CSF signaling is an intricate network of kinases and its substrates which change specificities depending upon the stimulus. In the event that Akt siRNA proves to be detrimental for the NSCs, experiments will be carried out using AKT1, AKT2, and AKT3 null mice. Alternatively, inducible RNAi systems will be used (Knockout Single Vector Inducible RNAi system, Clontech, Mountain View, Calif.) which allow regulating the expression of functional short hairpin RNAs (shRNAs) in mammalian cells for the purpose of silencing target genes. The system is designed so that expression of an shRNA is induced when either tetracycline (Tc) or doxycycline (Dox; a Tc derivative) is added to the culture medium. Induction of the shRNA results in suppression of the gene targeted by the shRNA through RNAi. An Akt inhibitor (ML9) and Clk/Sty inhibitor (TG003) may be used. To increase the transfection efficiency in cells, an inducible adenovirus PKCδII construct may be used, such as PKCδII cloned into the VIRAPOWER™ Adenoviral Expression System (Invitrogen, Carlsbad, Calif.) which contains the pAd/CMV/V5-DEST GATEWAY®-adapted (Invitrogen, Carlsbad, Calif.) adenoviral vector enabling high level protein expression from human cytomegalovirus (CMV) immediate-early enhancer/promoter.

Statistical analysis. Densitometric results from Western blots were analyzed with two-tailed t-tests when only two groups were compared. In other analyses where 3 groups were compared, one-way ANOVA followed by t-tests with Dunnett's corrections for multiple comparisons was utilized. All data was presented as mean±SEM. All statistical analysis of data was done via PRISM4 or PRISM5 statistical analysis software (GraphPad Prism, La Jolla, Calif.). Neurohistologic analyses are performed using ANOVA. All comparisons were considered significant at level of $P<0.05$.

Example 2

Computer in Silico Screening Identifies Potential G-CSF Mimetics

Schödinger 3D-modeling software (https://www.schrodinger.com/smdd/) was used to import a molecular model of G-CSF bound to its receptor from the NCBI protein database (PDB ID No. 1PGR_C; http://www.ncbi.nlm.nih.gov/protein/1PGR_C). The crystal structure coordinates showed a point of interaction whereby a glutamate (Glu20) from G-CSF protrudes into a small pocket of G-CSF-R, which was estimated to be a hydrogen bond accepting region. A molecule capable of interrupting this interaction could reduce binding of G-CSF with G-CSF-R. The first three compounds to be modeled in this system were those originally discovered by Kusano (*Blood* 2004, 103, 836-42), who reported their capacity to stimulate blood stem cell proliferation and to increase levels of circulating leukocytes in a rodent model. These three compounds were observed to fit a narrow binding pocket nestled between G-CSF and the G-CSF-R. The three compounds were able to occupy the pocket with negative but high estimated free energies of binding. The occlusion of the binding site would impede the ability of G-CSF to interact with G-CSF-R. The binding patterns indicated two points of binding that may be manipulated: two discrete binding sites at the protein-protein interface and binding into a pocket to disrupt the interaction of Glu20 from G-CSF with Tyr78 and Arg193 from G-CSF-R. Additional modeling identified 7 more compounds, 2 of which contained a similar pharmacaphore as the original Kusano compound whereas the other 5 were from an entirely different pharmacaphore. These compounds fit the binding pocket between the natural G-CSF ligand and its receptor. Compounds 1-5 were synthesized by the Moffitt Cancer Center Chemistry unit, whereas compounds 6-10 were purchased from Chembridge Corporation (San Diego, Calif.).

Example 3

Characterization of the Binding of [$^{125}$I]-G-CSF to its Receptor on Monocytes (THP-1 Cells) and Neuronal (SH-SY5Y) Cells Increasing concentrations of radio-labeled G-CSF (alone or in the presence of 100 fold excess "cold" G-CSF) were added to the cell cultures to generate saturation curves. Specific binding of [$^{125}$I]-G-CSF to receptors expressed in monocytes (THP-1 cells) revealed a Kd=57.49 pM and a Hill coefficient of 0.92. The Kd in the neuronal cell line (SH-SY5Y cells) was 607 pM with cooperative binding with a Hill coefficient of 2.7 (see TABLE 2).

TABLE 2

Specific Binding Parameters of [$^{125}$I]-G-CSF to its receptor on THP-1 cells and SH-SY5Y Cells.

| | Monocytic (THP-1) Cells | Neuronal (SH-SY5Y) Cells |
|---|---|---|
| Bmax | 901 pM | 4826 pM |
| Hill Coefficient | 1.19 | 2.71 |
| Kd | 53.8 pM | 608 pM |

The binding parameters, including dissociation constant (Kd), maximum binding capacity (Bmax), and the Hill Coefficient were calculated with GraphPad Prism 5 software by using nonlinear regression analysis.

Binding of the ligand with G-CSF receptors expressed by monocytic cells revealed greater affinity (lower Kd) than binding to the neuronal cells. However, binding of the ligand receptors expressed by the neuronal line exhibits substantial "cooperativity", indicated by Hill coefficient of 2.7 compared to 1.19 in the monocytic cell line. Cooperative binding refers to enhanced binding of ligand to a macromolecule when there are already other ligands present on the same macromolecule. The Hill coefficient describes the fraction of the receptor macromolecule saturated by ligand as a function of the ligand concentration; it is used to determine the degree of cooperative binding of the ligand to receptor. A coefficient of 1 indicates completely independent binding, regardless of how many additional ligands are already bound as demonstrated in the saturation curve of the monocytic cell line. Numbers greater than one indicate positive cooperativity, while numbers less than one indicate negative cooperativity.

Displacement studies were then conducted for each of the 10 compounds. A typical displacement study result is shown in FIG. 2 demonstrating the capacity of Compounds 6 and 10 to displace $^{125}$I-G-CSF from its receptor on monocytic cells with an IC50 of 13.7 nM and 2.3 nM, respectively. Four of the ten compounds tested were capable of significantly competing with G-CSF for binding on the receptor (FIG. 3A and FIG. 3B). Compounds 6 and 10, which displaced greater than 75% of the $^{125}$I-G-CSF, were further studied for their capacity to mimic or block the intracellular signaling triggered by the natural ligand.

Binding of G-CSF to its receptor triggers receptor homodimerization and activation of complex signal transduction and anti-apoptotic pathways which increase expression of STAT3, Bcl-2, and decrease expression of Bax. Previous work in our laboratory had shown that G-CSF upregulates expression of PKCδVIII and Bcl2 in human monocytic and neuronal cell cultures. G-CSF was added to the cell cultures and incubated for 24 hours. Whole cell lysates were immunoblotted for Bcl2 and PKCδVIII. Despite the much lower binding affinity of G-CSF for receptors expressed by neurons compared to binding affinity in monocytic cells, the expression of the anti-apoptotic protein Bcl2 and PKCδVIII, was much greater at equivalent concentrations (100 ng/mL or 5.3 nM) in the human neuronal cell line (FIG. 4A, FIG. 4B, FIG. 4C, and FIG. 4D). G-CSF, however, also increased the expression of PKCδVIII and Bcl2 in the monocytic line at a higher concentration (200 ng/mL or 10.6 nM).

Figure 5A:
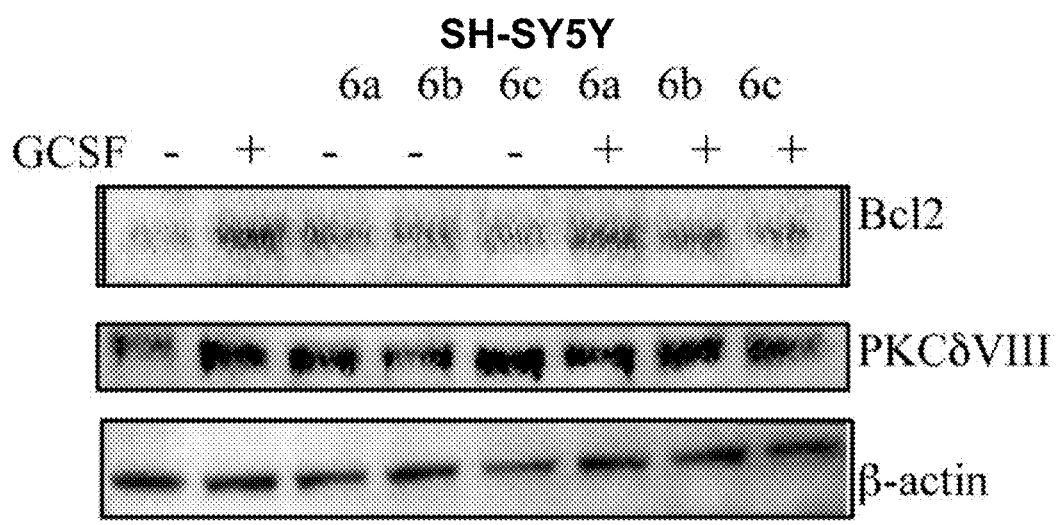
FIG. 5A, FIG. 5B, FIG. 5C, and FIG. 5D. Western blots of PKCδVIII and Bcl2 expressed in SH-SY5Y neuronal cells.
Figure 5B:
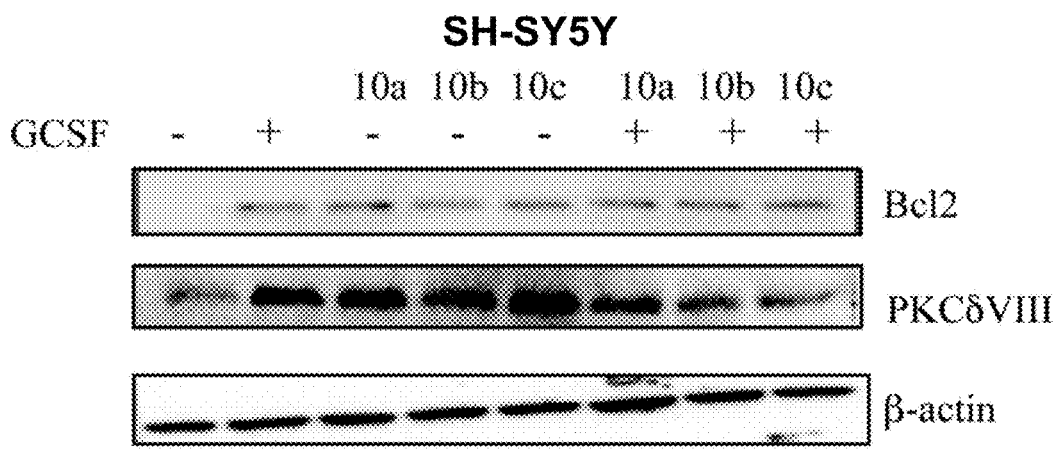
Figure 5C:
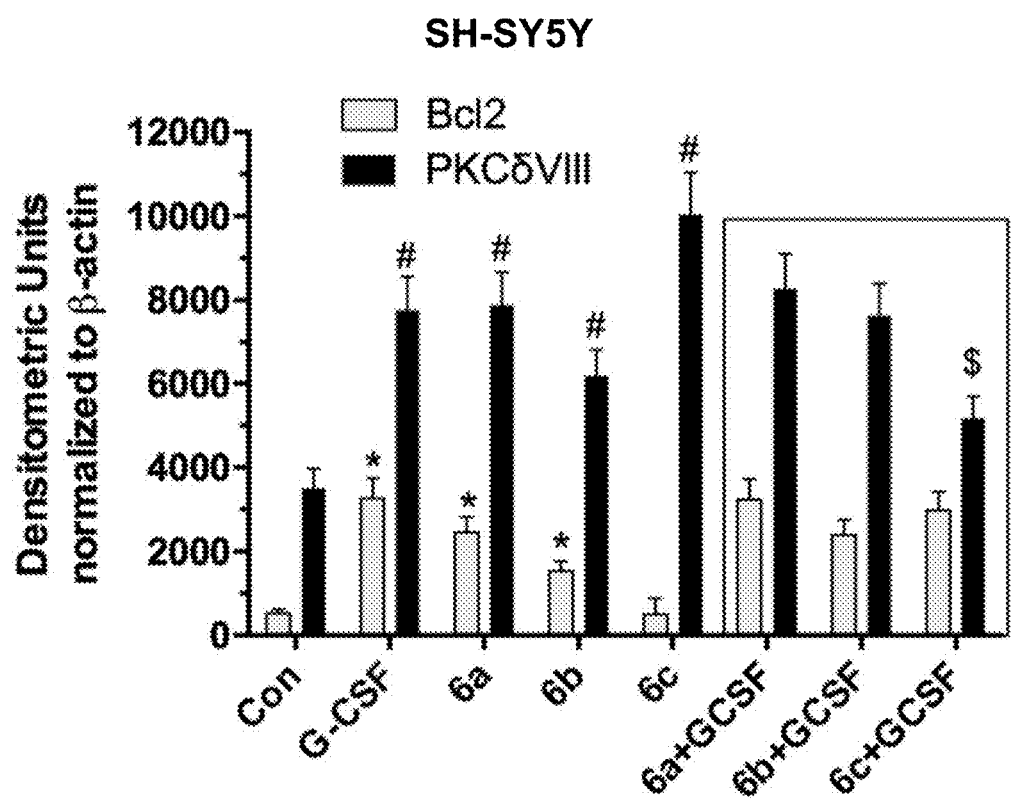

The two most effective competitors for the G-CSF receptor, Compounds 6 and 10 were evaluated for their capacity to activate or block the intracellular signaling triggered by G-CSF in human neuronal cells (SH-SY5Y) (FIG. 5A, FIG. 5B, FIG. 5C, and FIG. 5D). Incubation of human neuronal cells with Compound 6 alone significantly increased Bcl2 protein expression at the low and intermediate, but not the high concentration (FIG. 5C). In addition, Compound 6 alone stimulated PKCδVIII protein expression to levels equivalent to G-CSF alone. Incubation of the neuronal cells with both Compound 6 and G-CSF did not change the expression of either Bcl2 or PKCδVIII, indicating that Compound 6 did not act as an antagonist of G-CSF action in the neuronal cell line (FIG. 5C).

Figure 5D:
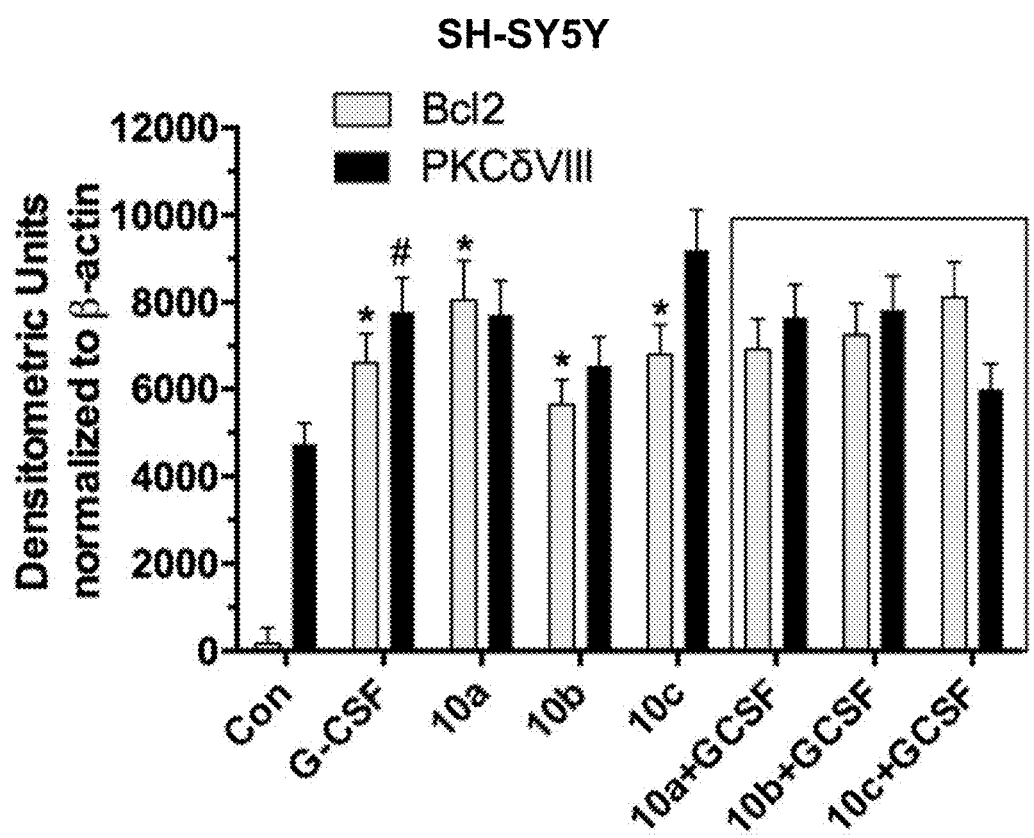

Incubation of the neuronal cell line with Compound 10 alone increased expression of both PKCδVIII and Bcl2 protein to levels equivalent to G-CSF alone (FIG. 5D). In addition, Compound 10 at all three concentrations tested did not block the actions of G-CSF. To summarize both Compound 6 and Compound 10 appear to act as agonists at the G-CSF receptor while Compound 6 at the highest concentration increases PKCδVIII without changing Bcl2 expression.

Figure 6A:
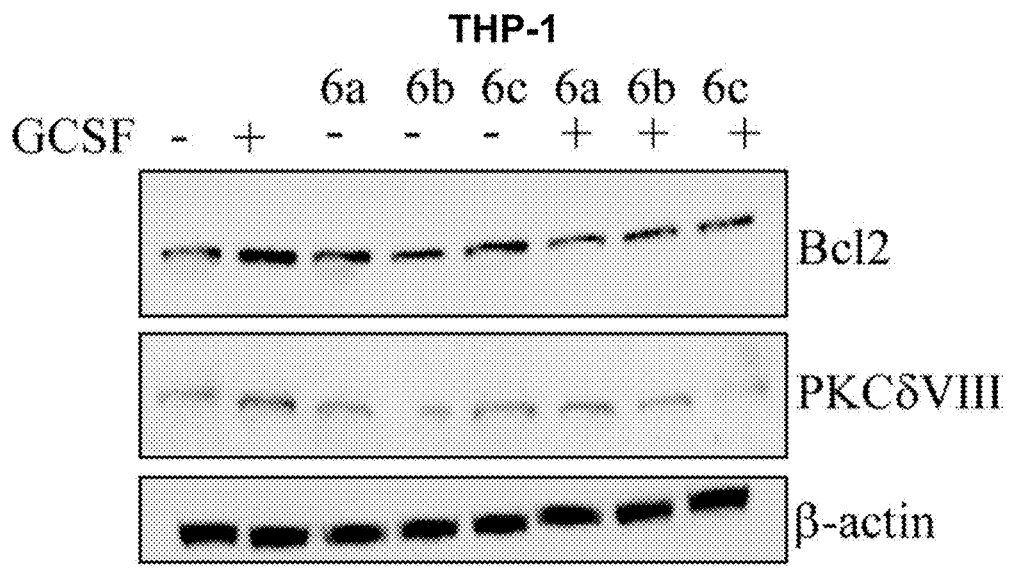
FIG. 6A, FIG. 6B, FIG. 6C, and FIG. 6D. Western blots of PKCδVIII and Bcl2 expressed in THP-1 monocytic cells.
Figure 6B:
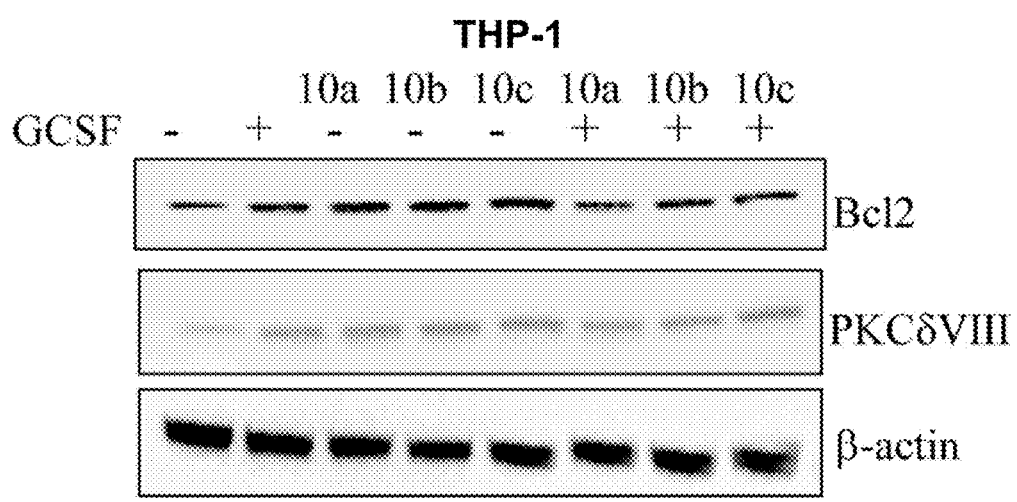
Figure 6C:
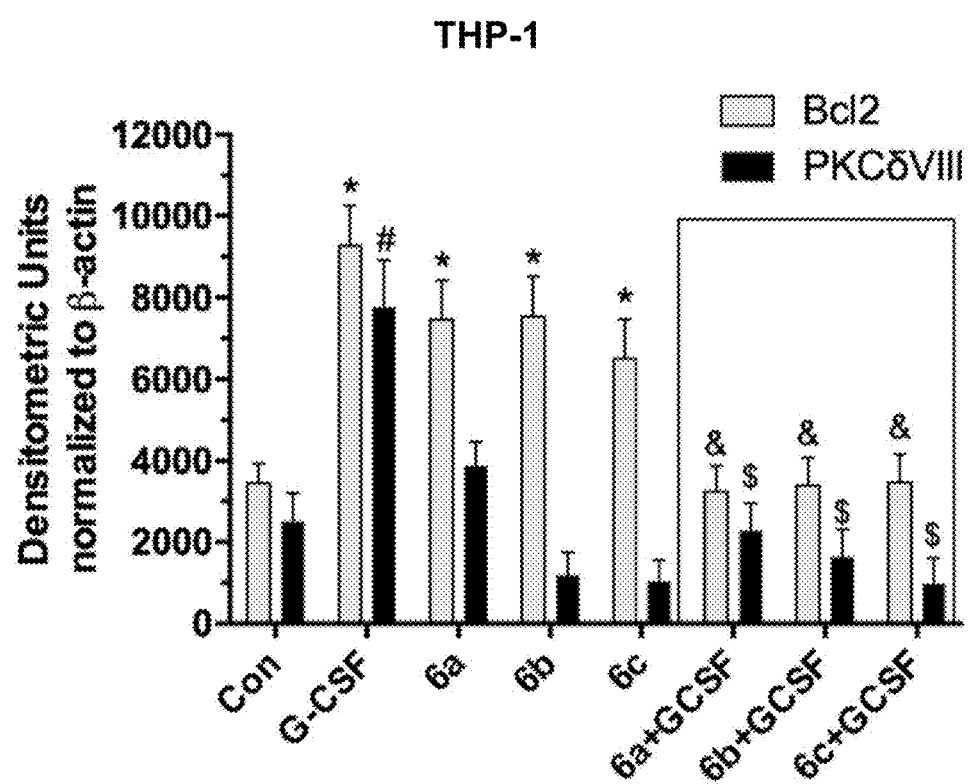
Figure 6D:
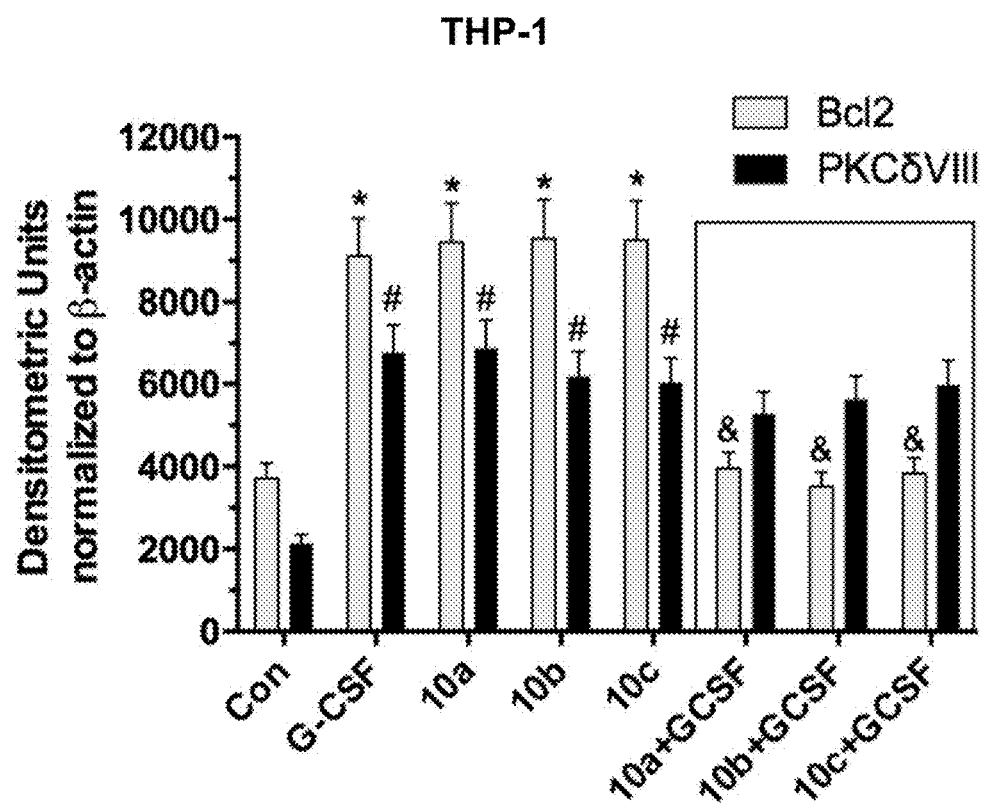

Studies in the monocytic THP-1 cell line revealed a different profile of drug-induced receptor activation (FIG. 6A, FIG. 6B, FIG. 6C, and FIG. 6D). Compound 6 alone increased expression of Bcl2, but not PKCδVIII at all 3 concentrations. Unlike the results in the neuronal cell line, addition of Compound 6 to G-CSF blocked the increase in Bcl2 and PKCδVIII protein expression (FIG. 6C). Hence, Compound 6 appears to act as a mixed agonist/antagonist in monocytic cell lines. Compound 10, at all 3 concentrations, was effective in significantly elevating expression of both Bcl2 and PKCδVIII (FIG. 6D). Compound 10 also appeared to act as a mixed agonist/antagonist by blocking the effects of G-CSF on Bcl2 expression. However, Compound 10 did not antagonize the effects on PKCδVIII protein expression.

Based on computer-based modeling of Compounds 1-3 and a search of drug libraries, we identified two pharmacophores with five analogues each for a total of ten compounds with potential to interact with the G-CSF receptor in human cell culture lines. Two of the ten drugs (Compound 6 and Compound 10) purchased from a commercial supplier were shown to interact with the G-CSF receptor and to trigger signal transduction in human monocytic and neuronal human cell cultures. Compound 10 appeared to function as a G-CSF agonist in neuronal cell lines. Both Bcl2 and PKCδVIII protein expression was increased by treatment with the drug in the neuronal cells. By contrast, Compound 10 at the lowest concentration antagonized the effects of G-CSF on the expression of Bcl2 and PKCδVIII in the monocytic cell lines. Therefore it may be possible to develop a combination drug (for example, G-CSF+Compound 10) that will serve as a neurotrophic factor in vivo, free of potentially dangerous leukocytosis. This could be accomplished by stimulating neurons that bear G-CSF receptor (for example, by both Compound 10 and G-CSF). At the same time Compound 10 would be capable of blocking the peripheral effects of G-CSF and thereby prevent excessive leukocytosis.

We have found compounds that mimic the neurotrophic and/or immune-modulating actions of G-CSF. The compounds are easier and cheaper to make than human G-CSF. Selective stimulation of central nervous system G-CSF receptors may be beneficial for treating some CNS diseases in which excessive generation of leukocytes and thrombocytes is an unwanted side effect. In addition, G-CSF receptor antagonists impermeable to brain may be useful in distinguishing peripheral from central actions of G-CSF. G-CSF antagonists may also be therapeutic for blood diseases associated with over-activity of the G-CSF system.

Example 4

Assessing the Capacity of Compounds to Mimic or Block the Intracellular Signaling Triggered by G-CSF Signal transduction induced by stimulation of the G-CSF Receptor. THP-1 cells or SH-SY5Y cells $3 \times 10^6$ cells in 5 mL media in a 25 $cm^2$ flask will be treated with 100 ng/mL G-CSF for 24 hours in the presence of increasing concentrations of the compounds to be tested. In parallel cultures, the compounds will be added to the cultures without G-CSF for 24 hours. Whole cell lysates (60 mg) will be separated on 10% polyacrylamide gel electrophoresis-SDS (PAGE-SDS). Proteins will be electrophoretically transferred to nitrocellulose membranes, blocked with Tris buffered saline, 0.1% Tween 20 containing 5% nonfat dried milk, washed, and incubated with a polyclonal antibody against either Bcl2 (Cell Signaling, Danvers, Mass.) or PKCδVIII (Chen, Y. K., et al. *J. Vasc. Surg.* 2008, 47, 1058-65). The house keeping gene GAPDH will be used as an internal standard. Following incubation with anti-rabbit IgG-HRP, enhanced chemiluminesence (Pierce™, Thermo Scientific, Waltham, Mass.) will be used for detection, and the gels will be analyzed using UN-SCAN-IT™ software (Silk Scientific, Inc., Orem, Utah).

Assessing the expression of PKCδII splice variants regulated by G-CSF. The effect of G-CSF in the presence of the test compounds or the effects of the test compounds alone on the expression of PKCδ isozymes in NSC will be studied. We will evaluate a dose curve to determine the optimal concentration. After 24 hours of incubation, total RNA will be extracted, and RT-PCR analysis will be performed with primers that simultaneously amplify PKCδI and PKCδII. Simultaneously, whole cell lysates will be harvested, and western blot analysis will be performed. Previous results indicate PKCδII increased Bcl2 and phosphorylation of BAD. We will evaluate the effect of G-CSF and the test compounds both at the RNA and protein level to decipher whether it is a transcriptional or translational effect. GAPDH levels will serve as an internal control.

In separate experiments, we will silence PKCδII (Ambion pre-designed siRNA, specificity determined in previous Patel publications) and then evaluate the test compounds. This will enable us to determine if additional pathways are activated to compensate for the loss of PKCδII. RT-qPCR and western blot analysis will be performed. We will also immunoblot for additional apoptosis indicators such as PARP and XIAP.

Further probing of signal transduction pathways induced by G-CSF receptor activation. To determine which signal transduction pathways are involved in G-CSF-mediated PKC (alternative splicing in neuronal cells, inhibitors of several signal transduction pathways will be applied. Inhibitors will be added 30 minutes prior to the addition of G-CSF or the test compounds. Signal transduction inhibitors to be used include the following: (a) LY29402 (a PI3K inhibitor); (b) Rapamycin (p70/85 S6 kinase inhibitor); (c) Herbimycin (a tyrosine kinase inhibitor); and (d) Ruxolitinib (JAK/STAT inhibitor). We will also determine the phosphorylation state of Akt kinase because it is a key downstream mediator of the PI3K pathway.

Once we determine the pathway involved, we will use pre-validated specific siRNAs for PI3K or JAK and STAT. 10 to 50 nM of siRNA will be transiently transfected for 48 to 72 hours into NSC and RT-PCR performed as described above. Scrambled siRNA will be used as control for off-target silencing. As such, the data will be evaluated using two separate approaches: one molecular and the other pharmacological.

In experiments in which LY294002 is added prior to incubation with G-CSF, we expect a decrease in phosphorylation of Akt kinase (Ser 473) with concurrent decreased PKCδII levels. We expect total Akt levels will remain the same, indicating that G-CSF mediated its effect via the PI3K→Akt pathway. Test compounds that reproduce the same signaling cascade will be considered to be agonists (or least partial agonists) of the G-CSF receptor. It is possible that a compound may have profound effects on PKCδII but lower effect on Bcl2. This may be due to the fact that additional pathways also activate Bcl2 cascade.

Example 5

In Vivo Expression of PKCδII in Mouse Brain Tissue from Mice that Undergo Controlled Cortical Impact (CCI)

Since G-CSF may increase neurogenesis via PKCδII (the mouse homolog of human PKCδVIII), we will determine the expression levels of PKCδII in mice treated with or without G-CSF. One cohort (n=6) of mice will receive G-CSF injections subcutaneously every other day for 2 weeks, and the other group will receive vehicle control (saline). In parallel experiments, 3 different concentrations of a test compound will be injected in mice daily for 1 week (6 mice per dose; total of 24 mice for the test compound). Brain tissue will be harvested, hippocampus dissected, followed by total RNA isolation for RT-PCR analysis. The primers will amplify PKCδI and PKCδII levels simultaneously. Western blot analysis will be performed on whole cell lysates as described above. We expect G-CSF will increase PKCδII expression levels in vivo, while PKCδI expression will remain unaffected. A compound as detailed herein with capacity to induce PKCδII in the NSC cultures should produce the same result.

Potential pitfalls and alternative approaches: The small molecule may fail to trigger signal transduction in brain tissue simply because it fails to cross the blood-brain-barrier. This can be tested by stereotaxic micro-injection of the drug into hippocampus or other brain region. If indeed direct injection of the test compound into brain reproduces the signal transduction effects of C-CSF administration, then the effects of the drug may be evident in the periphery. This can be assessed by measuring numbers of circulating hematopoietic stem cells (SCA-1+, c-kit+ cells), which may be significantly increased if it mimics the actions of G-CSF.

Example 6

Effects on Promotion of Recovery in a Hippocampal-dependent Task (RAWM) and on the Increased Expression of Neurotrophic Factors (BDNF and GDNF) in a Mouse Model of TBI G-CSF treatment significantly promoted recovery in the radial arm water maze (RAWM). We will test the capacity of compounds detailed herein to reproduce this effect. A cohort of C57BL6J mice will be trained in the RAWM. Then mice will undergo controlled cortical impact (CCI) described in Example 1. Mice will then be randomly assigned to 8 cohorts. Each cohort will be injected i.p. daily for 3 days with a test compound at 3 doses or vehicle and in combination with G-CSF (n=8 per dose; total 64 mice). See TABLE 3 for cohorts to be treated with Compound 6. Mice will be re-tested in the RAWM at one and two weeks after CCI before undergoing euthanasia. Before intracardiac perfusion, blood samples will be collected (to measure extent of leukocytosis and monocytosis). The brain will be perfused with PBS and phosphate-buffered paraformaldehyde, followed by dissection into right and left cortex, striatum, and hippocampus. These brain regions will be processed for measurements of two neurotrophic factors (BDNF, GDNF) and signal transduction assays (Bcl2 and PKCδII). Signal transduction and neurotrophic factor assays are described in Example 1, as well as the FACS protocol for counting blood leukocytes and monocytes. The same experimental protocol will be repeated with Compound 10.

TABLE 3

Effects on RAWM and Bcl2/PKCδIII expression.

| Cohorts | Treatment | Frequency | N |
|---------|-----------|-----------|---|
| A | Vehicle alone | 1 per day × 3 | 8 |
| B | G-CSF (100 μg/kg) + saline | 1 per day × 3 | 8 |
| C | Compound 6 (1 mg/kg) | 1 per day × 3 | 8 |
| D | Compound 6 (10 mg/kg) | 1 per day × 3 | 8 |
| E | Compound 6 (30 mg/kg) | 1 per day × 3 | 8 |
| F | G-CSF 100 μg/kg + Compound 6 (1 mg/kg) | 1 per day × 3 | 8 |
| G | G-CSF 100 μg/kg + Compound 6 (10 mg/kg) | 1 per day × 3 | 8 |
| H | G-CSF 100 μg/kg + Compound 6 (30 mg/kg) | 1 per day × 3 | 8 |

Total n = 64

The extent to which the test compound improves RAWM performance and activates G-CSF receptor-mediated signal transduction and increases expression of neurotrophic factors depends on how similar the biological activity of the drug mimics the natural ligand G-CSF, including its ability to access the CNS. Based on our cell culture data, Compound 10 administered alone will likely stimulate Bcl2 expression in both neural cells of brain and peripheral blood cells and hence one would see a very similar response as G-CSF alone. However when Compounds 10 is given with G-CSF, only the central nervous system effects will be observed. Hence it is theoretically possible to effect a direct central nervous system benefit by use of G-CSF plus Compound 10. In addition, Compound 6 will be studied in combination with G-CSF. We expect administration of Compound 6 will result in antagonism of G-CSF on peripheral cells while at the same time stimulate brain G-CSF receptors.

Failure of the drug to improve performance in the RAWM might reflect limited penetration of the drug into the CNS. An alternative approach would be to micro-inject the drug directly into hippocampus or striatum. If direct injection of the test compound into brain reproduces the effect of systemic G-CSF administration on signal transduction and neurotrophic factor expression, then, it may indicate that direct actions of G-CSF in brain (especially hippocampus) are necessary to enhance recovery in the RAWM. In other words, it may suggest that the actions of G-CSF on its receptor in the periphery (bone marrow cells) may not be paramount for mediating beneficial effects in brain. Pharmacokinetic studies to determine plasma half-life and extent of penetration into CNS may be done.

Example 7

Effects on Hippocampal Neurogenesis and Microgliosis In Vivo Following TBI

Following controlled cortical impact (CCI) on day 0, Mice C57BL6J will be randomly assigned to 8 cohorts. All mice will be injected with 75 mg/kg bromodeoxyuridine (BrdU) i.p. daily x 3 days along with the test drug (with and without G-CSF as shown in TABLE 4 for cohorts to be treated with Compound 6).

Two weeks after the last dose of G-CSF or drug (enough time for newly born cells to differentiate into neurons), mice will be euthanized, animals perfused, and the brain dissected into right and left frontal cortex, striatum, and hippocampus. Tissue is then prepared for cryosectioning and immunohistology. Methods for immunostaining, stereologic estimates of neurogenesis and measurement of microgliosis are described in Example 1. The same experimental protocol will be repeated with Compound 10.

TABLE 4

Effects on Neurogenesis and Microgliosis.

| Cohorts | Treatment | Frequency | N |
|---|---|---|---|
| A | Vehicle alone | 1 per day x 3 | 8 |
| B | G-CSF (100 µg/kg) + saline | 1 per day x 3 | 8 |
| C | Compound 6 (1 mg/kg) | 1 per day x 3 | 8 |
| D | Compound 6 (10 mg/kg) | 1 per day x 3 | 8 |
| E | Compound 6 (30 mg/kg) | 1 per day x 3 | 8 |
| F | G-CSF 100 µg/kg + Compound 6 (1 mg/kg) | 1 per day x 3 | 8 |
| G | G-CSF 100 µg/kg + Compound 6 (10 mg/kg) | 1 per day x 3 | 8 |
| H | G-CSF 100 µg/kg + Compound 6 (30 mg/kg) | 1 per day x 3 | 8 |
| | | Total n = | 64 |

The total number of BrdU+ nuclei will be significantly increased in mice treated with (1) G-CSF or (2) Compound 6 alone, or (3) Compound 10 alone, indicating that the G-CSF or its mimetics stimulate neural stem/progenitor cell proliferation. Co-administration of Compound 6 with G-CSF will result in antagonism of G-CSF on peripheral cells while at the same time stimulating brain G-CSF receptors. By counting the total number of doubly-labeled BrdU+/NeuN (neuron-specific nuclear protein) nuclei, G-CSF treatment or G-CSF mimetics will significantly increase number of new neurons in hippocampus compared to vehicle-treated mice.

The test compound may fail to stimulate neurogenesis simply because it fails to cross the blood-brain-barrier. This can be tested by stereotaxic micro-injection of the drug into hippocampus. If indeed direct injection of the test compound into brain reproduces the neurogenic effects of C-CSF administration, then the structure of the compound may be modified to make it permeable to brain.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. A method of treating a condition in a subject, the method comprising administering a compound to the subject, wherein the compound is according to Formula I:

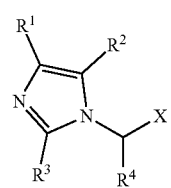

(I)

wherein $R^1$ and $R^2$ are each hydrogen, or $R^1$ and $R^2$ together with the carbon atoms to which they are attached form a phenyl ring; $R^3$ and $R^4$ are each hydrogen, or $R^3$ and $R^4$ together with the atoms to which they are attached form a six-membered heterocyclic ring, wherein the ring is unsubstituted or substituted with one substituent selected from amino, nitro, methyl, ethyl, and hydroxyl; X is —$C(R^5)(R^6)$-phenyl wherein the phenyl is substituted with $R^7$ and $R^8$, or X is indole substituted with 0, 1, 2, or 3 $R^9$, or X is pyrazole substituted with phenyl wherein the phenyl is substituted with 0, 1, 2, or 3 $R^{10}$; $R^5$ and $R^6$ are each independently selected from hydrogen, hydroxyl, $C_1$-$C_4$ alkyl, and $C_1$-$C_4$ alkoxy, or $R^5$ and $R^6$ together form an oxo group; $R^7$ is hydrogen, hydroxyl, $C_1$-$C_{12}$ alkyl, or $C_1$-$C_{12}$ alkoxy; $R^8$ is halogen, hydroxyl, $C_1$-$C_4$ alkyl, or $C_1$-$C_4$ alkoxy; each $R^9$ is independently halogen, hydrogen, hydroxyl, $C_1$-$C_4$ alkyl, $C_1$-$C_4$ alkoxy, amino, or nitro; and each $R^{10}$ is independently halogen, hydroxyl, $C_1$-$C_4$ alkyl, $C_1$-$C_4$ alkoxy, amino, or nitro, or the compound is according to Formula II:

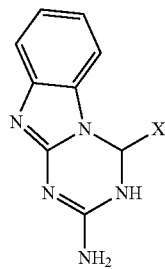

(II)

wherein X is indole substituted with 0, 1, 2, or 3 $R^9$, or X is pyrazole substituted with phenyl wherein the phenyl is substituted with 0, 1, 2, or 3 $R^{10}$; each $R^9$ is independently halogen, hydrogen, hydroxyl, $C_1$-$C_4$ alkyl, $C_1$-$C_4$ alkoxy, amino, or nitro; and each $R^{10}$ is independently halogen, hydrogen, hydroxyl, $C_1$-$C_4$ alkyl, $C_1$-$C_4$ alkoxy, amino, or nitro, or the compound is according to Formula III:

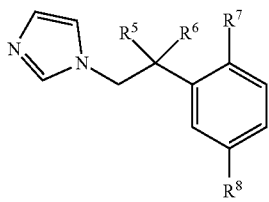

(III)

wherein $R^5$ and $R^6$ are independently hydrogen, hydroxyl, methyl, ethyl, methoxy, or ethoxy, or $R^5$ and $R^6$ together form an oxo group; $R^7$ is hydrogen, hydroxyl, $C_1$-$C_{12}$ alkyl, or $C_1$-$C_{12}$ alkoxy; and $R^8$ is halogen, hydrogen, hydroxyl, $C_1$-$C_4$ alkyl, or $C_1$-$C_4$ alkoxy, and wherein the condition is selected from the group consisting of neurodegenerative disease, stroke, traumatic brain injury (TBI), impaired motor function, and impaired cognitive function.

Clause 2. The method of clause 1, wherein the neurodegenerative disease is selected from the group consisting of Alzheimer's Disease (AD), amyotrophic lateral sclerosis (ALS), Parkinson's Disease (PD), prion disease, motor neuron disease, Huntington's Disease, spinocerebellar ataxia, and spinal muscular atrophy.

Clause 3. A method of stimulating the central nervous system Granulocyte Colony-Stimulating Factor (G-CSF) Receptor in a subject, the method comprising administering a compound to the subject, wherein the compound is according to Formula I:

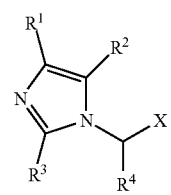

(I)

wherein $R^1$ and $R^2$ are each hydrogen, or $R^1$ and $R^2$ together with the carbon atoms to which they are attached form a phenyl ring; $R^3$ and $R^4$ are each hydrogen, or $R^3$ and $R^4$ together with the atoms to which they are attached form a six-membered heterocyclic ring, wherein the ring is unsubstituted or substituted with one substituent selected from amino, nitro, methyl, ethyl, and hydroxyl; X is —C($R^5$)($R^6$)-phenyl wherein the phenyl is substituted with $R^7$ and $R^8$, or X is indole substituted with 0, 1, 2, or 3 $R^9$, or X is pyrazole substituted with phenyl wherein the phenyl is substituted with 0, 1, 2, or 3 $R^{10}$; $R^5$ and $R^6$ are each independently selected from hydrogen, hydroxyl, $C_1$-$C_4$ alkyl, and $C_1$-$C_4$ alkoxy, or $R^5$ and $R^6$ together form an oxo group; $R^7$ is hydrogen, hydroxyl, $C_1$-$C_{12}$ alkyl, or $C_1$-$C_{12}$ alkoxy; $R^8$ is halogen, hydrogen, hydroxyl, $C_1$-$C_4$ alkyl, or $C_1$-$C_4$ alkoxy; each $R^9$ is independently halogen, hydrogen, hydroxyl, $C_1$-$C_4$ alkyl, $C_1$-$C_4$ alkoxy, amino, or nitro; and each $R^{10}$ is independently halogen, hydrogen, hydroxyl, $C_1$-$C_4$ alkyl, $C_1$-$C_4$ alkoxy, amino, or nitro, or the compound is according to Formula II:

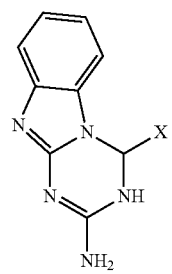

(II)

wherein X is indole substituted with 0, 1, 2, or 3 $R^9$, or X is pyrazole substituted with phenyl wherein the phenyl is substituted with 0, 1, 2, or 3 $R^{10}$; each $R^9$ is independently halogen, hydrogen, hydroxyl, $C_1$-$C_4$ alkyl, $C_1$-$C_4$ alkoxy, amino, or nitro; and each $R^{10}$ is independently halogen, hydrogen, hydroxyl, $C_1$-$C_4$ alkyl, $C_1$-$C_4$ alkoxy, amino, or nitro, or the compound is according to Formula III:

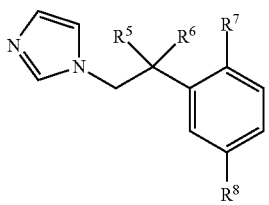

(III)

wherein $R^5$ and $R^6$ are independently hydrogen, hydroxyl, methyl, ethyl, methoxy, or ethoxy, or $R^5$ and $R^6$ together form an oxo group; $R^7$ is hydrogen, hydroxyl, $C_1$-$C_{12}$ alkyl, or $C_1$-$C_{12}$ alkoxy; and $R^8$ is halogen, hydrogen, hydroxyl, $C_1$-$C_4$ alkyl, or $C_1$-$C_4$ alkoxy.

Clause 4. The method of any one of clauses 1-3, wherein the compound is of Formula I, and wherein $R^1$ and $R^2$ are each hydrogen.

Clause 5. The method of any one of clauses 1-3, wherein the compound is of Formula I, and wherein $R^1$ and $R^2$ together with the carbon atoms to which they are attached form a phenyl ring.

Clause 6. The method of any one of clauses 1-3, wherein the compound is of Formula I, and wherein $R^3$ and $R^4$ are each hydrogen.

Clause 7. The method of any one of clauses 1-3, wherein the compound is of Formula I, and wherein $R^3$ and $R^4$ together with the atoms to which they are attached form a six-membered heterocyclic ring, wherein the ring is unsubstituted or substituted with one substituent selected from amino, nitro, methyl, ethyl, and hydroxyl.

Clause 8. The method of clause 7, wherein the six-membered heterocyclic ring is substituted with amino or nitro.

Clause 9. The method of any one of clauses 1-3, wherein the compound is of Formula I, and wherein X is —C($R^5$)($R^6$)-phenyl wherein the phenyl is substituted with $R^7$ and $R^8$.

Clause 10. The method of any one of clauses 1-3, wherein the compound is of Formula I or Formula III, and wherein $R^5$ and $R^6$ are each independently hydroxyl or methyl.

Clause 11. The method of any one of clauses 1-3, wherein the compound is of Formula I or Formula III, and wherein $R^5$ and $R^6$ together form an oxo group.

Clause 12. The method of any one of clauses 1-3, wherein the compound is of Formula I or Formula III, and wherein $R^7$ is hydroxyl or $C_1$-$C_{12}$ alkoxy.

Clause 13. The method of clause 12, wherein $R^7$ is hydroxyl.

Clause 14. The method of any one of clauses 1-3, wherein the compound is of Formula I or Formula III, and wherein $R^8$ is halogen.

Clause 15. The method of clause 14, wherein halogen is Cl.

Clause 16. The method of any one of clauses 1-3, wherein the compound is of Formula I or Formula II, and wherein X is indole substituted with 0, 1, 2, or 3 $R^9$.

Clause 17. The method of clause 16, wherein each $R^9$ is independently halogen or methoxy.

Clause 18. The method of any one of clauses 1-3, wherein the compound is of Formula I or Formula II, and wherein X is pyrazole substituted with phenyl, wherein the phenyl is substituted with 0, 1, 2, or 3 $R^{10}$.

Clause 19. The method of clause 18, wherein each $R^{10}$ is independently hydroxyl, methoxy, or nitro.

Clause 20. The method of any one of the previous clauses, wherein the compound decreases amyloid burden, enhances neurogenesis, enhances synaptogenesis, or enhances cognitive performance, or a combination thereof.

Clause 21. The method of any one of the previous clauses, wherein the compound binds the Granulocyte Colony-Stimulating Factor (G-CSF) Receptor.

Clause 22. The method of any one of the previous clauses, wherein the compound displaces at least 50% of G-CSF from the G-CSF receptor.

Clause 23. The method of clause 6, wherein the compound displaces at least 75% of G-CSF from the G-CSF receptor.

Clause 24. The method of any one of the previous clauses, wherein the compound is a peripheral antagonist of the G-CSF receptor.

Clause 25. The method of any one of the previous clauses, wherein the compound is a central agonist of G-CSF receptor.

Clause 26. The method of any one of the previous clauses, wherein expression of Bcl2 is increased.

Clause 27. The method of any one of the previous clauses, wherein expression of PKCδVIII is increased.

Clause 28. The method of any one of the previous clauses, wherein expression of STAT3 is increased.

Clause 29. The method of any one of the previous clauses, wherein expression of Bax is decreased.

Clause 30. The method of any one of the previous clauses, wherein leukopoiesis is minimally affected or is not affected.

Clause 31. The method of any one of clauses 1-3 and 20-30, wherein the compound is selected from the following:

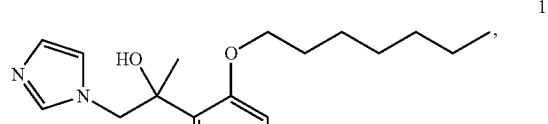

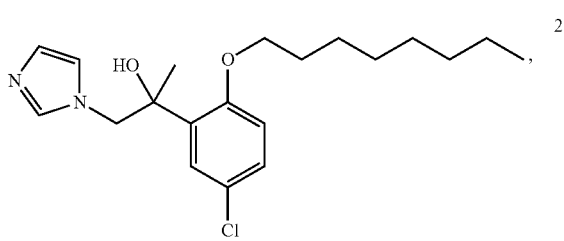

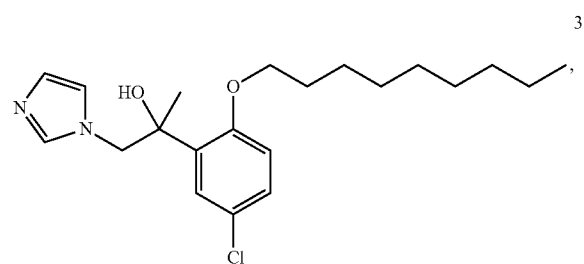

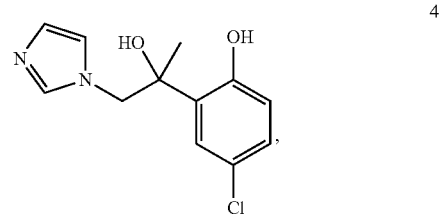

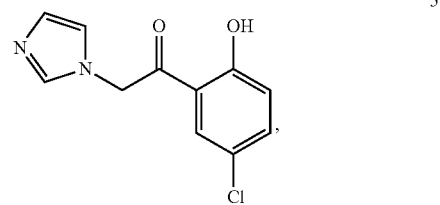

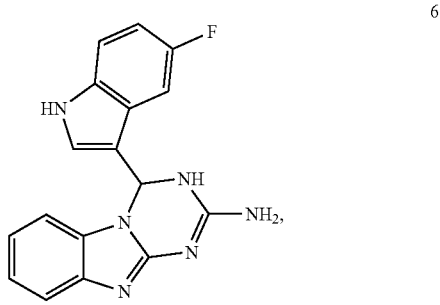

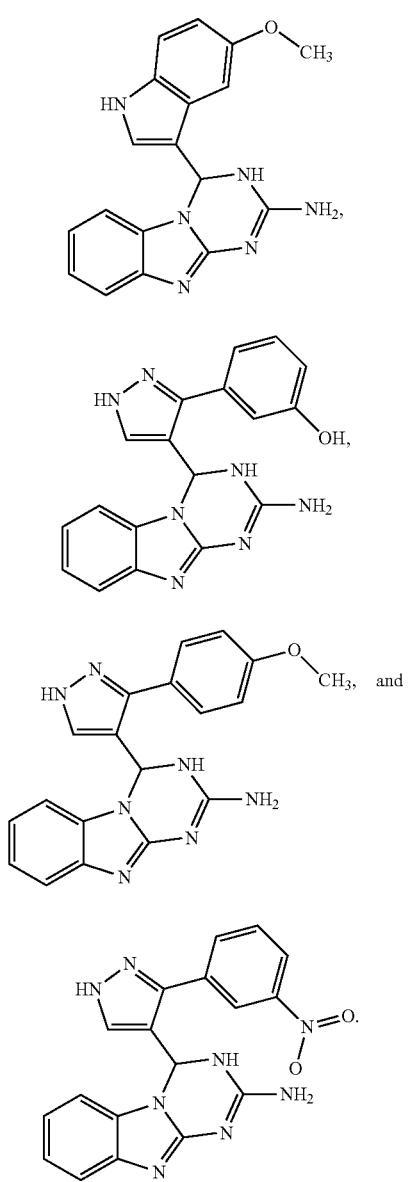
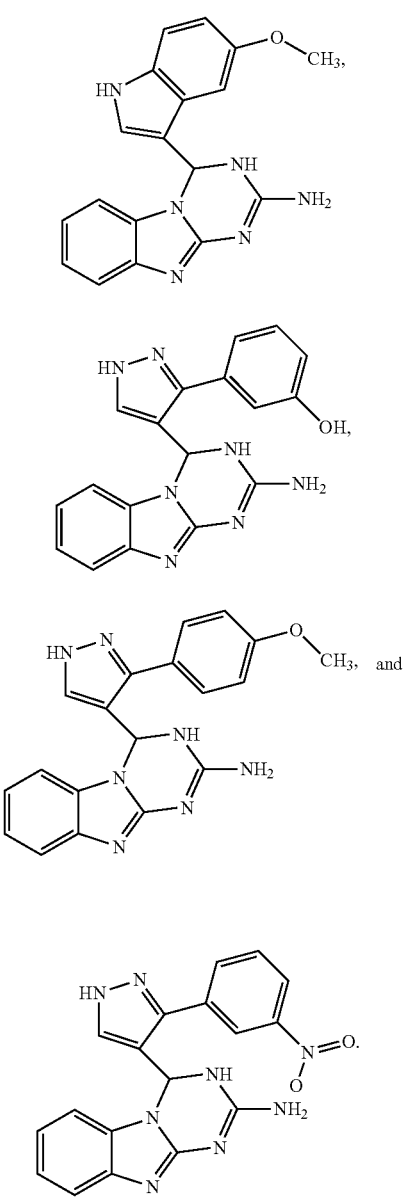
Clause 32. The method of any one of clauses 1-3 and 20-30, wherein the compound is selected from the following:
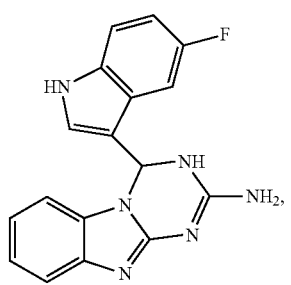
Clause 33. The method of any one of clauses 1-3 and 20-30, wherein the compound is selected from the following:
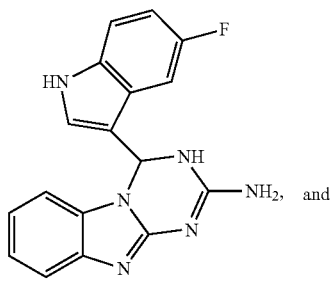

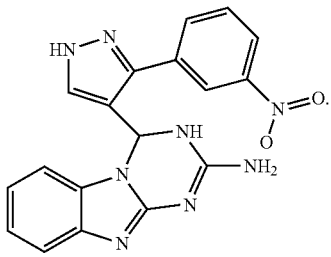

Clause 34. The method of any one of the above clauses, wherein the compound is co-administered with a G-CSF polypeptide.

Clause 35. The method of clause 34, wherein the G-CSF polypeptide comprises an amino acid sequence of SEQ ID NO: 1.

Clause 36. The method of clause 34, wherein the G-CSF polypeptide is encoded by a polynucleotide of SEQ ID NO: 2

Clause 37. A compound selected from the following:

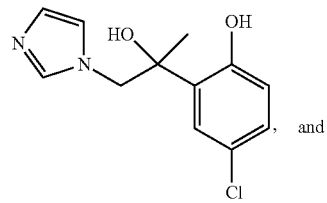

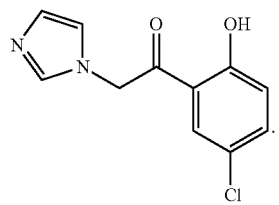

| SEQUENCES |
|---|
| Polypeptide sequence of human G-CSF. Accession No. CAA27291 |
| SEQ ID NO: 1 |
| 1   MAGPATQSPM KLMALQLLLW HSALWTVQEA TPLGPASSLP QSFLLKCLEQ VRKIQGDGAA |
| 61  LQEKLVSECA TYKLCHPEEL VLLGHSLGIP WAPLSSCPSQ ALQLAGCLSQ LHSGLFLYQG |
| 121 LLQALEGISP ELGPTLDTLQ LDVADFATTI WQQMEELGMA PALQPTQGAM PAFASAFQRR |
| 181 AGGVLVASHL QSFLEVSYRV LRHLAQP |
| Polynucleotide sequence of human G-CSF (mRNA). Accession No. E01219 |
| SEQ ID NO: 2 |
| 1    ggagcctgca gcccagcccc acccagaccc atggctggac ctgccaccca gagccccatg |
| 61   aagctgatgg ccctgcagct gctgctgtgg cacagtgcac tctggacagt gcaggaagcc |
| 121  accccctgg gccctgccag ctccctgccc cagagcttcc tgctcaagtg cttagagcaa |
| 181  gtgaggaaga tccagggcga tggcgcagcg ctccaggaga agctgtgtgc cacctacaag |
| 241  ctgtgccacc ccgaggagct ggtgctgctc ggacactctc tgggcatccc ctgggctccc |
| 301  ctgagcagct gccccagcca ggccctgcag ctgcaggct gcttgagcca actccatagc |
| 361  ggccttttcc tctaccaggg gctcctgcag gccctggaag ggatctcccc cgagttgggt |
| 421  cccaccttgg acacactgca gctggacgtc gccgactttg ccaccaccat ctggcagcag |
| 481  atggaagaac tgggaatggc ccctgccctg cagcccaccc agggtgccat gccggccttc |
| 541  gcctctgctt ccagcgccg ggcaggaggg gtcctagttg cctcccatct gcagagcttc |
| 601  ctggaggtgt cgtaccgcgt tctacgccac cttgcccagc cctgagccaa gccctcccca |
| 661  tcccatgtat ttatctctat ttaatattta tgtctattta agcctcatat ttaaagacag |
| 721  ggaagagcag aacggagccc caggcctctg tgtccttccc tgcatttctg agtttcattc |
| 781  tcctgcctgt agcagtgaga aaaagctcct gtcctcccat ccctggact gggaggtaga |
| 841  taggtaaata ccaagtattt attactatga ctgctcccca gccctggctc tgcaatgggc |
| 901  actgggatga gccgctgtga gcccctggtc ctgagggtcc ccacctggga cccttgagag |
| 961  tatcaggtct cccacgtggg agacaagaaa tccctgttta atatttaaac agcagtgttc |
| 1021 cccatctggg tccttgcacc cctcactctg gcctcagccg actgcacagc ggcccctgca |
| 1081 tccccttggc tgtgaggccc ctggacaagc agaggtggcc agagctggga ggcatggccc |

| SEQUENCES |
|---|

```
1141  tggggtccca cgaatttgct ggggaatctc gttttttcttc ttaagacttt tgggacatgg 1201  tttgactccc gaacatcacc gacgcgtctc ctgtttttct gggtggcctc gggacacctg 1261  ccctgccccc acgagggtca ggactgtgac tcttttttagg gccaggcagg tgcctggaca 1321  tttgccttgc tggacgggga ctggggatgt gggagggagc agacaggagg aatcatgtca 1381  ggcctgtgtg tgaaaggaag ctccactgtc accctccacc tcttcacccc ccactcacca 1441  gtgtcccctc cactgtcaca ttctaactga acttcaggat aataaagtgc ttgcctccaa 1501  aaaaaaaaaa aaaaaaaaa a
```

Polypeptide sequence of human G-CSF-R
Accession No. Q99062

SEQ ID NO: 3

```
  1  MARLGNCSLT WAALIILLLP GSLEECGHIS VSAPIVHLGD PITASCIIKQ NCSHLDPEPQ

61  ILWRLGAELQ PGGRQQRLSD GTQESIITLP HLNHTQAFLS CCLNWGNSLQ ILDQVELRAG

121  YPPAIPHNLS CLMNLTTSSL ICQWEPGPET HLPTSFTLKS FKSRGNCQTQ GDSILDCVPK

181  DGQSHCCIPR KHLLLYQNMG IWVQAENALG TSMSPQLCLD PMDVVKLEPP MLRTMDPSPE

241  AAPPQAGCLQ LCWEPWQPGL HINQKCELRH KPQRGEASWA LVGPLPLEAL QYELCGLLPA

301  TAYTLQIRCI RWPLPGHWSD WSPSLELRTT ERAPTVRLDT WWRQRQLDPR TVQLFWKPVP

361  LEEDSGRIQG YVVSWRPSGQ AGAILPLCNT TELSCTFHLP SEAQEVALVA YNSAGTSRPT

421  PVVFSESRGP ALTRLHAMAR DPHSLWVGWE PPNPWPQGYV IEWGLGPPSA SNSNKTWRME

481  QNGRATGFLL KENIRPFQLY EIIVTPLYQD TMGPSQHVYA YSQEMAPSHA PELHLKHIGK

541  TWAQLEWVPE PPELGKSPLT HYTIFWTNAQ NQSFSAILNA SSRGFVLHGL EPASLYHIHL

601  MAASQAGATN STVLTLMTLT PEGSELHIIL GLFGLLLLLT CLCGTAWLCC SPNRKNPLWP

661  SVPDPAHSSL GSWVPTIMEE DAFQLPGLGT PPITKLTVLE EDEKKPVPWE SHNSSETCGL

721  PTLVQTYVLQ GDPRAVSTQP QSQSGTSDQV LYGQLLGSPT SPGPGHYLRC DSTQPLLAGL

781  TPSPKSYENL WFQASPLGTL VTPAPSQEDD CVFGPLLNFP LLQGIRVHGM EALGSF
```

---

We claim:

1. A method of treating a condition in a subject, the method comprising administering a compound to the subject, wherein the compound is

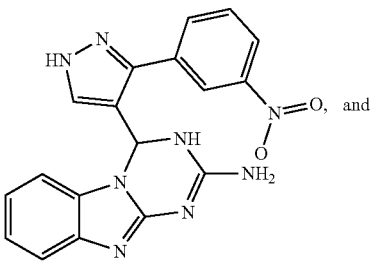

wherein the condition is selected from the group consisting of neurodegenerative disease, stroke, traumatic brain injury (TBI), impaired motor function, and impaired cognitive function.

2. The method of claim 1, wherein the neurodegenerative disease is selected from the group consisting of Alzheimer's Disease (AD), amyotrophic lateral sclerosis (ALS), Parkinson's Disease (PD), prion disease, motor neuron disease, Huntington's Disease, spinocerebellar ataxia, and spinal muscular atrophy.

3. The method of claim 1, wherein the compound decreases amyloid burden, enhances neurogenesis, enhances synaptogenesis, or enhances cognitive performance, or a combination thereof.

4. The method of claim 1, wherein the compound binds the Granulocyte Colony-Stimulating Factor (G-CSF) Receptor.

5. The method of claim 1, wherein the compound displaces at least 50% of G-CSF from the G-CSF receptor.

6. The method of claim 1, wherein the compound is a peripheral antagonist of the G-CSF receptor.

7. The method of claim 1, wherein the compound is a central agonist of G-CSF receptor.

8. The method of claim 1, wherein expression of Bcl2 is increased.

9. The method of claim 1, wherein expression of PKCδVIII is increased.

10. The method of claim 1, wherein expression of Bax is decreased.

11. The method of claim 1, wherein leukopoiesis is minimally affected or is not affected.

12. The method of claim 1, wherein the compound is co-administered with a G-CSF polypeptide.

* * * * *

UNITED STATES PATENT AND TRADEMARK OFFICE
CERTIFICATE OF CORRECTION

PATENT NO. : 10,376,495 B2
APPLICATION NO. : 15/821634
DATED : August 13, 2019
INVENTOR(S) : Juan Sanchez-Ramos et al.

It is certified that error appears in the above-identified patent and that said Letters Patent is hereby corrected as shown below:

On the Title Page

Item (71), Column 1 (Applicants), Line 8, delete "INSTRITUTE" and insert -- INSTITUTE --.

Signed and Sealed this
Twenty-second Day of November, 2022

Katherine Kelly Vidal
*Director of the United States Patent and Trademark Office*

SEQUENCE LISTING

<160> NUMBER OF SEQ IDS: 3

<210> SEQ ID NO 1
<211> LENGTH: 207
<212> TYPE: PRT
<213> ORGANISM: Homo sapiens

<400> SEQUENCE: 1

```
Met Ala Gly Pro Ala Thr Gln Ser Pro Met Lys Leu Met Ala Leu Gln
 1               5                  10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
```

```
            85                  90                  95
Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 2
<211> LENGTH: 1521
<212> TYPE: DNA
<213> ORGANISM: Homo sapiens

<400> SEQUENCE: 2
ggagcctgca gcccagcccc acccagaccc atggctggac ctgccaccca gagccccatg     60
aagctgatgg ccctgcagct gctgctgtgg cacagtgcac tctggacagt gcaggaagcc    120 accccctgg ccctgccag ctccctgccc cagagcttcc tgctcaagtg cttagagcaa      180
gtgaggaaga tccagggcga tggcgcagcg ctccaggaga agctgtgtgc cacctacaag    240
ctgtgccacc ccgaggagct ggtgctgctc ggacactctc tgggcatccc ctgggctccc    300
ctgagcagct gccccagcca ggccctgcag ctggcaggct gcttgagcca actccatagc    360 ggcctttcc tctaccaggg gctcctgcag gccctggaag ggatctcccc cgagttgggt     420
cccaccttgg acacactgca gctggacgtc gccgactttg ccaccaccat ctggcagcag    480
atggaagaac tgggaatggc ccctgccctg cagcccaccc agggtgccat gccggccttc    540
gcctctgctt tccagcgccg ggcaggaggg gtcctagttg cctcccatct gcagagcttc    600
ctggaggtgt cgtaccgcgt tctacgccac cttgcccagc cctgagccaa gccctcccca    660
tcccatgtat ttatctctat ttaatattta tgtctattta agcctcatat ttaaagacag    720
ggaagagcag aacggagccc caggcctctg tgtccttccc tgcatttctg agtttcattc    780
tcctgcctgt agcagtgaga aaaagctcct gtcctcccat ccctggact gggaggtaga     840 taggtaaata ccaagtattt attactatga ctgctcccca gccctggctc tgcaatgggc    900
actgggatga gccgctgtga gccctggtc tgagggtcc ccacctggga cccttgagag      960
tatcaggtct cccacgtggg agacaagaaa tccctgttta atatttaaac agcagtgttc   1020
cccatctggg tccttgcacc cctcactctg gcctcagccg actgcacagc ggcccctgca   1080
tccccttggc tgtgaggccc ctggacaagc agaggtggcc agagctggga ggcatggccc   1140
tggggtccca cgaatttgct ggggaatctc gttttcttc ttaagacttt tgggacatgg    1200
tttgactccc gaacatcacc gacgcgtctc ctgttttcct gggtggcctc gggacacctg   1260
ccctgccccc acgagggtca ggactgtgac tcttttagg gccaggcagg tgcctggaca    1320
tttgccttgc tggacgggga ctggggatgt ggagggagc agacaggagg aatcatgtca    1380
ggcctgtgtg tgaaaggaag ctccactgtc accctccacc tcttcacccc ccactcacca   1440
```

```
gtgtcccctc cactgtcaca ttctaactga acttcaggat aataaagtgc ttgcctccaa    1500
aaaaaaaaaa aaaaaaaaaa a                                              1521
```

<210> SEQ ID NO 3
<211> LENGTH: 836
<212> TYPE: PRT
<213> ORGANISM: Homo sapiens

<400> SEQUENCE: 3

```
Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
            20                  25                  30

Ala Pro Ile Val His Leu Gly Asp Pro Ile Thr Ala Ser Cys Ile Ile
        35                  40                  45

Lys Gln Asn Cys Ser His Leu Asp Pro Glu Pro Gln Ile Leu Trp Arg
    50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
        115                 120                 125

Leu Ser Cys Leu Met Asn Leu Thr Thr Ser Ser Leu Ile Cys Gln Trp
    130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
    210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285

Ala Leu Gln Tyr Glu Leu Cys Gly Leu Leu Pro Ala Thr Ala Tyr Thr
    290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335

Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
```

-continued

```
            355                 360                 365
Gln Gly Tyr Val Val Ser Trp Arg Pro Ser Gln Ala Gly Ala Ile
370                 375                 380
Leu Pro Leu Cys Asn Thr Thr Glu Leu Ser Cys Thr Phe His Leu Pro
385                 390                 395                 400
Ser Glu Ala Gln Glu Val Ala Leu Val Ala Tyr Asn Ser Ala Gly Thr
                405                 410                 415
Ser Arg Pro Thr Pro Val Val Phe Ser Glu Ser Arg Gly Pro Ala Leu
            420                 425                 430
Thr Arg Leu His Ala Met Ala Arg Asp Pro His Ser Leu Trp Val Gly
                435                 440                 445
Trp Glu Pro Pro Asn Pro Trp Pro Gln Gly Tyr Val Ile Glu Trp Gly
            450                 455                 460
Leu Gly Pro Pro Ser Ala Ser Asn Ser Asn Lys Thr Trp Arg Met Glu
465                 470                 475                 480
Gln Asn Gly Arg Ala Thr Gly Phe Leu Leu Lys Glu Asn Ile Arg Pro
                485                 490                 495
Phe Gln Leu Tyr Glu Ile Ile Val Thr Pro Leu Tyr Gln Asp Thr Met
                500                 505                 510
Gly Pro Ser Gln His Val Tyr Ala Tyr Ser Gln Glu Met Ala Pro Ser
            515                 520                 525
His Ala Pro Glu Leu His Leu Lys His Ile Gly Lys Thr Trp Ala Gln
                530                 535                 540
Leu Glu Trp Val Pro Glu Pro Pro Glu Leu Gly Lys Ser Pro Leu Thr
545                 550                 555                 560
His Tyr Thr Ile Phe Trp Thr Asn Ala Gln Asn Gln Ser Phe Ser Ala
                565                 570                 575
Ile Leu Asn Ala Ser Ser Arg Gly Phe Val Leu His Gly Leu Glu Pro
            580                 585                 590
Ala Ser Leu Tyr His Ile His Leu Met Ala Ala Ser Gln Ala Gly Ala
            595                 600                 605
Thr Asn Ser Thr Val Leu Thr Leu Met Thr Leu Thr Pro Glu Gly Ser
            610                 615                 620
Glu Leu His Ile Ile Leu Gly Leu Phe Gly Leu Leu Leu Leu Leu Thr
625                 630                 635                 640
Cys Leu Cys Gly Thr Ala Trp Leu Cys Cys Ser Pro Asn Arg Lys Asn
                645                 650                 655
Pro Leu Trp Pro Ser Val Pro Asp Pro Ala His Ser Ser Leu Gly Ser
            660                 665                 670
Trp Val Pro Thr Ile Met Glu Glu Asp Ala Phe Gln Leu Pro Gly Leu
            675                 680                 685
Gly Thr Pro Pro Ile Thr Lys Leu Thr Val Leu Glu Glu Asp Glu Lys
            690                 695                 700
Lys Pro Val Pro Trp Glu Ser His Asn Ser Ser Glu Thr Cys Gly Leu
705                 710                 715                 720
Pro Thr Leu Val Gln Thr Tyr Val Leu Gln Gly Asp Pro Arg Ala Val
                725                 730                 735
Ser Thr Gln Pro Gln Ser Gln Ser Gly Thr Ser Asp Gln Val Leu Tyr
            740                 745                 750
Gly Gln Leu Leu Gly Ser Pro Thr Ser Pro Gly Pro Gly His Tyr Leu
            755                 760                 765
Arg Cys Asp Ser Thr Gln Pro Leu Leu Ala Gly Leu Thr Pro Ser Pro
770                 775                 780
```

```
Lys Ser Tyr Glu Asn Leu Trp Phe Gln Ala Ser Pro Leu Gly Thr Leu
785                 790                 795                 800

Val Thr Pro Ala Pro Ser Gln Glu Asp Asp Cys Val Phe Gly Pro Leu
                805                 810                 815

Leu Asn Phe Pro Leu Leu Gln Gly Ile Arg Val His Gly Met Glu Ala
            820                 825                 830

Leu Gly Ser Phe
        835
```